United States Patent
Shatz et al.

(10) Patent No.: US 8,071,314 B2
(45) Date of Patent: Dec. 6, 2011

(54) IMMUNOCELLULAR RECEPTORS RELATED TO NEUROLOGICAL DISORDERS AND THERAPEUTIC USES THEREOF

(75) Inventors: Carla J. Shatz, Boston, MA (US); Joshua Syken, Jamaica Plain, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1179 days.

(21) Appl. No.: 10/321,704

(22) Filed: Dec. 16, 2002

(65) Prior Publication Data

US 2003/0170690 A1 Sep. 11, 2003

Related U.S. Application Data

(60) Provisional application No. 60/340,595, filed on Dec. 14, 2001.

(51) Int. Cl.
*G01N 33/567* (2006.01)
*G01N 33/48* (2006.01)
(52) U.S. Cl. ............ 435/7.1; 435/7.21; 436/503; 436/63
(58) Field of Classification Search ........................ None
See application file for complete search history.

(56) References Cited

U.S. PATENT DOCUMENTS

| | | | | |
|---|---|---|---|---|
| 5,185,250 | A | * | 2/1993 | Brenner et al. ............... 435/69.3 |
| 5,935,803 | A | * | 8/1999 | Vasquez et al. ................. 435/15 |
| 6,011,018 | A | * | 1/2000 | Crabtree et al. ................ 514/31 |
| 6,030,833 | A | * | 2/2000 | Seebach et al. ............... 435/325 |
| 6,110,735 | A | * | 8/2000 | Chartier et al. ............ 435/320.1 |
| 6,291,659 | B1 | | 9/2001 | Carosella et al. ............ 536/23.1 |
| 6,384,203 | B1 | * | 5/2002 | Anderson et al. ............ 536/23.5 |
| 6,416,973 | B1 | * | 7/2002 | Bakker et al. ................ 435/69.1 |
| 2004/0072256 | A1 | * | 4/2004 | Mandelboim et al. ......... 435/7.2 |

FOREIGN PATENT DOCUMENTS

WO  WO 03/051834  6/2003

OTHER PUBLICATIONS

Corriveau et al., Neuron, vol. 21, 505-520, Sep. 1998.*
G. Huh et al., *Science*, vol. 290, pp. 2155-2159, 2000.
G. Dennis, Jr. et al., *J. Immun.*, pp. 6371-6377, 1999.

* cited by examiner

*Primary Examiner* — Daniel C Gamett

(74) *Attorney, Agent, or Firm* — Edwards Angell Palmer & Dodge LLP; David G. Conlin; Melissa Hunter-Ensor, Esq.

(57) ABSTRACT

Class I major histocompatibility complex, is required in the activity-dependent refinement and plasticity of connections in the developing and adult central nervous system, demonstrating that molecules can perform critical roles in both systems. Similarities in the cellular signaling mechanisms of the immune and nervous systems provide for development of therapeutic and diagnostic agents in abnormal neuronal cellular function.

6 Claims, 14 Drawing Sheets

GP49 A,B in situ

Digr1 in situ p3 p26 p30

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 1
gatgtsaccc tgaggtgctg                                          20

<210> SEQ ID NO 2

```
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
ggcatgtgta mytctgctcc                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (1)..(2)
<223> OTHER INFORMATION: a, t, c or g
<220> FEATURE:
<221> NAME/KEY: modified_base
<222> LOCATION: (5)
<223> OTHER INFORMATION: a, t, c or g

<400> SEQUENCE: 3
nngtnggcta ygtkgacrac                                              20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 4
kyrggtyytc rttcaggg                                                18

<210> SEQ ID NO 5
<211> LENGTH: 2526
<212> TYPE: DNA
<213> ORGANISM: Mus musculus

<400> SEQUENCE: 5
atgtcctgca ccttcacagc cctgctctgt cttggactga ctctgagcct ctggatccca    60
gtgctgacag ggtccctccc taagcctatc ctcagagtac agccagactc tgtggtctcc   120
aggtggacta aggtgacttt cttttgtgag agacaattg gagccaatga gtaccgcctc   180
tataaagatg gaaagctata taaaactgta acaaagaaca acagaagcc agcaaacaag   240 gctgaattct cactctcaaa tgtagacctg agtaatgcag gtcaatatga atgttcctac   300
agcacccagt ataaatcatc aggctacagt gacccctga gctggtggt gacaggacac   360 tactggacac ccagcctttt agcccaagcc agccctgtgg taacttcagg agggtatgtc   420
accctccagt gtgagtcctg gcacaacgat cacaagttca ttctgactgt agaaggacca   480
cagaagctct cgtggacaca agactcacag tataattact ctacaaggaa gtaccacgcc   540
ctgttctctg tgggccctgt gacccccaac cagagatgga tatgcagatg ttacagttat   600
gacaggaaca gaccatatgt gtggtcacct ccaagtgaat ccgtggagct cctggtctca   660
ggtaatctcc aaaaccaac catcaaggct gaaccaggat ctgtgatcac ctccaaaaga   720
gcaatgacca tctggtgtca ggggaacctg gatgcagaag tatattttct gcataatgag   780
ggaagccaaa aacacagag cacacagacc tacagcagc tgggaacaa gggcaagttc   840 ttcatcccct tctatgacaag acaacatgca gggcaatatc gctgttattg ttacggctca   900
```

```
gctggttggt cacagcccag tgacaccctg gagctggtgg tgacaggaat ctatgaacac    960
tataaaccca ggctgtcagt actgcccagc cctgtggtga cagcaggagg aaacatgaca   1020
ctccactgtg cctcagactt tcactacgat aaattcattc tcaccaagga agataagaaa   1080
ttcggcaact cactggacac agagcatata tcttctagta gacagtaccg agccctgttt   1140
attataggac ccacaacccc aacccataca gggacattca gatgttatgg ttacttcaag   1200
aatgccccac agctgtggtc agtacctagt gatctccaac aaatactcat ctcagggctg   1260
tccaagaagc cctctctgct gactcaccaa ggccatatcc tggaccctgg aatgaccctc   1320
accctgcagt gttactctga catcaactat gacagatttg ctctgcacaa ggtgggggga   1380
gctgacatca tgcagcactc tagccagcag actgacactg gcttctctgt ggccaacttc   1440
acactgggct atgtgagtag ctccactgga ggccaataca gatgctatgg tgcacacaac   1500
ctttcctctg agtggtcagc ctccagtgag cccctggaca tcctgatcac aggacagctc   1560
cctctcactc cttccctctc agtgaagcct aaccacacag tgcactcagg agagaccgtg   1620
agcctgctgt gttggtcaat ggactctgtg gatactttca ttctgtccaa ggagggatca   1680
gcccagcaac ccctacgact aaaatcaaag tcccatgatc agcagtccca ggcagaattc   1740
tccatgagtg ctgtgacctc ccatctctca gcgacctaca ggtgctatgg tgctcaaaac   1800
tcatctttct acctcttgtc atctgccagt gcccctgtgg agctcacagt ctcaggaccc   1860
atcgaaacct ctacccccgcc agggacaatg tccatgccac taggtggact gcatatgtac   1920
ctgaaggctc tcattggagt gtctgtggcc ttcatcctgt tcctcttcat cctcatcttc   1980
attcttctcc gacgaagaca tcggggaaaa ttcaggaaag atgtccagaa agagaaagac   2040
ttgcaacttt cttcaggagc tgaagagccc ataaccagga aaggagaact ccagaagagg   2100
cccaacccag ctgctgccac ccaggaagaa agcctatatg cttcagtgga ggacatgcaa   2160
actgaggatg gagtggagct gaacagctgg acaccacctg aggaagatcc cagggagag    2220
acttatgccc aggtgaaacc ctccaggctc aggaaggcag gacatgtctc accttctgtc   2280
atgtcaaggg aacaactgaa cacagaatat gaacaagcag aagagggcca aggagcaaac   2340
aatcaggctg ccgaatctgg ggagtcccag gatgtgacct atgcccagct gtgcagcagg   2400
acactcagac aggggcagc tgcatctcct ctctcccagg caggggaagc cccagaggag    2460
cccagtgtat atgctactct ggcggctgct cgtccagagg ctgttcccaa ggatgtggag   2520
caatga                                                              2526
```

IMMUNOCELLULAR RECEPTORS RELATED TO NEUROLOGICAL DISORDERS AND THERAPEUTIC USES THEREOF

The present application claims the benefit of U.S. provisional application No. 60/340,595, filed Dec. 14, 2001, which is incorporated by reference, herein, in its entirety.

BACKGROUND OF THE INVENTION

1. Field of the Invention

Immune system genes and their cognate receptors, have a functional role in the wiring and function of the nervous system. Specific brain functions for immune related molecules and cognate receptor systems include memory functions and other processes occurring in the brain both in development and adulthood that are referred to as "synaptic plasticity". Drugs commonly used to treat autoimmune diseases, infection or tissue rejection associated with transplantation will have therapeutic action in the treatment of disorders of the Central Nervous System (CNS). These drugs function to alter the interaction of neurons expressing immune related molecules, Gp49, PIR, PIRA, PIRB, LIR, NKR-P1, NKp46, Digr1, ILT, MIR, KIR, class I MHC and other immune-related receptors.

2. Background

Diversity in the immune system is used to establish an essentially unlimited array of complex receptor-ligand interactions. In B cells, the interactions occur between the variable region of antibodies and different antigens. In T cells, the interactions occur between the variable region of T cell receptors (TCRs) and cell surface proteins encoded by a set of genes termed the major histocompatibility complex (MHC). MHC molecules play an essential role in immunologic diversity by presenting on the cell surface peptides that are derived from intracellular proteolysis; these peptides can then in turn be recognized by TCRs. There are two different types of MHC molecules: class I, which present peptides to cytotoxic T cells (CD8+ cells), and class II, which present peptides to helper T cells (CD4+ cells). MHC I molecules function classically as heterotrimers consisting of a heavy chain, which presents peptide, and an invariant light chain, termed β2-microglobulin. TCRs function as heterodimers that associate with a number of integral membrane signaling proteins and are important in maintaining the integrity of the immune system.

Neuronal cells, including brain cells are non-dividing cells and there is little in the understanding of the complex networks that exist between cells of the nervous system. The mechanisms that cause many neurological disorders are poorly understood. It would be of major benefit if molecules involved in neurological disorders, neural networking and regeneration of nerve cells, could be identified.

SUMMARY OF THE INVENTION

It is an object of the present invention to identify immune related receptors and ligands involved in neuronal disorders, provide methods of treating and diagnosing neural disorders, and provide methods for identifying compounds for use as part of therapeutic and/or diagnostic methods.

In particular, the present invention relates, first, to the identification of the functional association of class I MHC with neuronal disorders, normal brain development and memory mechanisms. Class I MHC was identified using pan-specific MHC probes and was found to be expressed by neurons in specific patterns and at specific times throughout the brain.

The invention further comprises the identification of the CD3 gene expression in neuronal cells and its function in normal brain development and memory mechanisms.

The invention also comprises the identification of the presence of mRNA for several activating and inhibitory receptors and receptor systems for Class I MHC, used by lymphocytes and other immune cells. In the immune system, similar receptors can either bind class I MHC directly or alter class I MHC signaling mechanisms. The identified immune-related receptors include, but are not limited to Gp49, PIR, PIRA, PIRB, LIR, NKR-P1, NKp46, Digr1, ILT, MIR, KIR and the like.

In particular, the invention provides for methods for identifying drugs which inhibit, regulate or activate the interactions between the Class I MHC, the immune-related receptors and ligands thereof. This is useful in determining the therapeutic value of drugs and/or identification of novel drugs involved in neuronal disorders. For example: drugs for treating neurological diseases and disorders such as all agonists and antagonists that are known or designed to interact with Class I MHC and either the known receptors of Class I MHC or novel Class I MHC receptors present in neurons or the downstream signaling pathways. The invention fully encompasses use of immunosuppressive drugs for the treatment of neurodegenerative disorders, (such as Parkinson's; Alzheimer's) or autoimmune disorders (multiple sclerosis) of the central nervous system.

The invention encompasses methods for identifying compounds capable of modulating the expression of the mammalian Class I MHC and the immune-related gene receptors, and/or the synthesis or activity of the mammalian such gene products, wherein such methods comprise contacting a compound to a cell that expresses, for example, a class I MHC gene, measuring the level of class I MHC gene expression, gene product expression or gene product activity, and comparing this level to the level of class I MHC gene expression, gene product expression, expression patterns thereof, or gene product activity produced by the cell in the absence of the compound, such that if the level obtained in the presence of the compound differs from that obtained in its absence, a compound capable of modulating the expression of the mammalian class I MHC gene and/or the synthesis or activity of the mammalian class I MHC gene products has been identified.

In accordance with the invention, drugs, which modulate the expression of MHC genes can be used to for treatments for enhancing memory or reduce memory loss, especially in traumatized patients. Examples of such immune modulating drugs are, for example, cytokines known to induce Class I MHC expression in tissues, including neurons can also play a role in memory, autoimmune disorders of the brain, neuronal reaction to viral infection and narcolepsy/sleep disorders, immunophilins, FK506 and the like.

In another embodiment, methods of treatment of neurological disorders include: isolating, purifying, culturing neural stem cells and progenitor cells with appropriate drugs and screening of the neural stem cells or their progeny for the desired expression patterns of the class I MHC and other immune-related receptors prior to transplantation into patients.

The invention further comprises methods for the treatment of mammalian MHC mediated neuropsychiatric and other neuronal disorders resulting from abnormal MHC and other immune related receptor expression, wherein such methods comprise supplying the mammal with a nucleic acid molecule encoding normal gene products such that unimpaired MHC or other immune related receptors are expressed and symptoms of the disorder are ameliorated.

The invention further comprises methods for the treatment of mammalian MHC mediated neuropsychiatric and other neuronal disorders resulting from abnormal MHC and other immune related receptor gene mutations, wherein such methods comprise supplying the mammal with a cell comprising a nucleic acid molecule that encodes an unimpaired MHC or other immune related receptor gene products such that the cell expresses the unimpaired MHC or other immune related receptor gene products and symptoms of the disorder are ameliorated.

The invention further comprises methods for the treatment of mammalian immune related molecule mediated neuropsychiatric and other neuronal disorders resulting from abnormal immune related molecule and other immune related receptor expression, wherein such methods comprise supplying the mammal with a nucleic acid molecule encoding normal gene products such that immune related molecule or other immune related receptors are expressed and symptoms of the disorder are ameliorated.

The invention further comprises methods for the treatment of mammalian immune related molecule mediated neuropsychiatric and other neuronal disorders resulting from abnormal immune related molecule and other immune related receptor gene mutations, wherein such methods comprise supplying the mammal with a cell comprising a nucleic acid molecule that encodes an immune related molecule or other immune related receptor gene products such that the cell expresses the immune related molecule or other immune related receptor gene products and symptoms of the disorder are ameliorated.

In addition, the present invention comprises methods that utilize the MHC or other immune related receptors gene and/or gene product sequences for the diagnostic evaluation, genetic testing and prognosis of a Class I MHC-mediated neuronal disorder. For example, the invention comprises methods for diagnosing disorders wherein neuronal cells have abnormal pattern expressions or lack expression of class I MHC or other immune related receptors. Such methods comprise measuring the above gene expression in a patient sample, or detecting an MHC mutations in the genome of the mammal suspected of exhibiting such a disorder.

The invention also comprises the discovery that part of the T-cell receptor (TCR) beta locus is expressed by neurons of the mammalian CNS in vivo, using in situ hybridization methods with probes specific for the two TCR beta constant regions. Surprisingly, TCR is expressed by neurons in olfactory bulb, thalamus, hypothalamus, and cortex of newborn mice. Unspliced T-cell receptor genes were also found to be present in neurons.

Other aspects of the invention are discussed infra.

BRIEF DESCRIPTION OF THE FIGURES

FIG. 1A shows the expression of class I MHC transcripts in coronal sections of the mouse CNS at P6 and P40 and in a cross section of P6 eye. Left column, adjacent Nissl-stained section; middle column, hybridization with antisense riboprobe under dark-field optics; right column, hybridization with control sense probe. D, dorsal; L, lateral; hc, hippocampus; ctx, neocortex; gcl, ganglion cell layer. Arrowheads and dashed lines indicate dLGN. Scale bar for P6 and P40 brains, 0.5 mm; scale bar for P6 eye, 250 µm. FIG. 1B shows expression of CD3ζ in the dorsal lateral geniculate nucleus (dLGN) during eye-specific layer formation. Upper panel, adjacent Nissl-stained coronal section of P6 mouse brain (arrowhead, dLGN). Middle panel, hybridization with CD3ζ antisense probe (dashed lines, dLGN); hybridization is also present in the ventroposterior nucleus of thalamus (down and to right of dLGN). The lower panel shows excess of unlabeled competitor probe(cptr). Scale bar, 200 µm.

FIGS. 3A-3E and 3G are photographs of tissue sections showing the abnormal retinogeniculate projections but normal dLGN ultrastructure in mice deficient in class I MHC signaling. At P12, one eye was injected with horse radish peroxidase-conjugated wheat germ agglutinate (WGA-HRP); after 1 day, anterograde axonal transport results in labeling of the entire retinal projection to the LGN. Labeling pattern in the dLGN is shown in bright-field optics (label is black) or as dark-field composites [label is white]. FIG. 3A is a representative projection from retina to dLGN contralateral (dashed lines; coronal section; dorsal is up; lateral is left) or ipsilateral to eye injected with WGA-HRP (asterisks indicate labeled area from ipsilateral eye: lateral is to right) in a P13 $\beta_2M^{+/+}$ wild-type mouse and a $\beta_2M^{-/-}$ mutant mouse. FIGS. 3B and 3C are representative (3B) and extreme (3C) examples of the projection from the ipsilateral eye observed in $\beta_2M^{-/-}$ TAP1−/− mice. FIG. 3F is a graph of areas (±SEM) occupied by the ipsilateral retinal projection to the LGN for $\beta_2M^{+/+}$ (wild-type), $\beta_2M^{-/-}$, $\beta_2M^{-/-}$TAP1$^{-/-}$, and CD3ζ$^{-/-}$ mice, normalized to total dLGN area. The ipsilateral projection area in $\beta_2M^{+/+}$ animals is set as 100% (horizontal dashed line). Asterisks indicate significant differences from $\beta_2M^{+/+}$ mice (P<0.05, Student's two-tailed t test). FIG. 3G is an electron micrograph of the dLGN from a $\beta_2M^{-/-}$TAP1$^{-/-}$ mouse (at P24), showing a typical R-type synaptic bouton (R) making contacts with a dendrite (d). A well-myelinated axon (ax) is also present in this field. Scale bar, 1 µm.

FIGS. 4A-4D are graphs showing the enhanced hippocampal LTP in mice deficient either for cell surface class I MHC expression or for CD3z. FIG. 4A shows field excitatory postsynaptic potential (fEPSP) slopes in wild-type versus CD3ζ$^{-/-}$-deficient mice. Tetanus was applied at time 0. (Insets) Superimposed sample fEPSPs recorded 10 min before or 180 min after tetanic stimulation from individual wild-type (left) and CD3ζ$^{-/-}$, (right) slices. Scale bar, 10 msec/0.25 mV. FIG. 4B shows the N-methyl-D aspartate (NMDA) receptor dependence of LTP in CD3ζ deficient mice. Tetanus was applied at time 0 either in the absence [filled circles; from (A)] or presence (hollow circles) of 50 µM D-APV. All points in (A) and (B) are averages of four consecutive fEPSPs (means±SEM, normalized to 15-min baseline) recorded from CA1. FIG. 4 D is a graph showing the relation (logarithmic plot) between synaptic enhancement and stimulation frequency. Points at 0.033 Hz (test pulse frequency) indicate baseline values (horizontal dashed line). Points at 100 Hz are taken from (C). Values in (C) and (D) are mean fEPSP slopes for each genotype over the 1-hour period following tetanus.

FIG. 5B illustrates the TCR beta genomic locus and brain-derived transcript and FIG. 5C illustrates the predicted hypothetical JB2 2.7 protein.

DETAILED DESCRIPTION OF THE INVENTION

Figure 1:
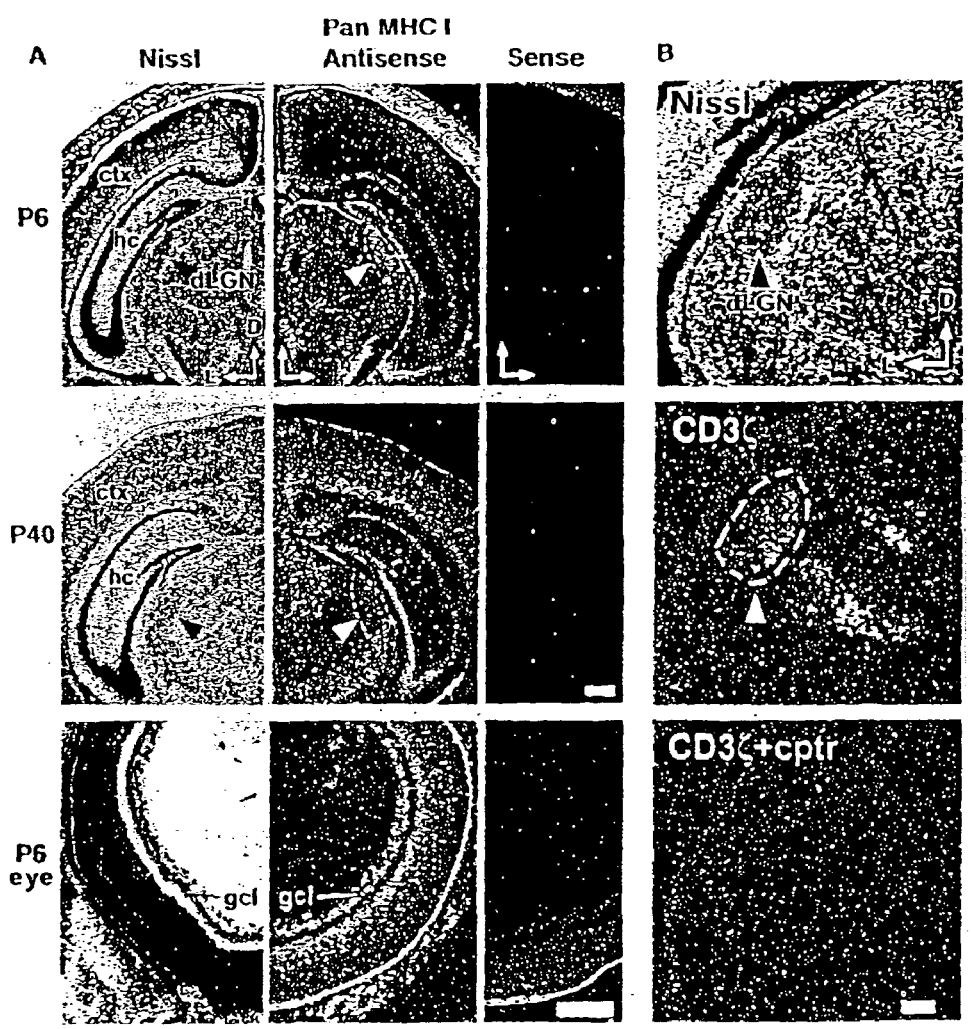
FIGS. 1A and 1B are photographs of tissue sections showing Class I MHC expression in mouse CNS.

The invention comprises the identification, screening, diagnosis and treatment of neural disorders. The invention further comprises the identification, and screening of drugs that influence the immune system for treatment of disorders of the Central Nervous System (CNS). These drugs function to alter the interaction of neurons expressing immune related molecules, including, but not limited to Gp49, PIR, PIRA, PIRB, LIR, NKR-P1, NKp46, Digr1, ILT, MIR, KIR, class I MHC other immune-related receptors.

Definitions

The following definitions are provided for specific terms which are used in the following written description.

As used herein, "a", "an," and "the" include plural references unless the context clearly dictates otherwise. For example, a reference to "a class I MHC polypeptide" includes a plurality of class I MHC polypeptides.

As used herein, a "small molecule" is usually less than about 10K in molecular weight and may possess a number of physicochemical and pharmacological properties which enhance cell penetration, allow it to resist degradation and prolong its physiological half-life. Preferably, small molecules are not immunogenic.

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

As used herein, the term "administering a molecule to a cell" (e.g., an expression vector, nucleic acid, cytokines, angiogenic factors, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

As used herein, "immunoreceptors" will refer to class I MHC(HLA-A, -B, -C, -G) and the like) and other immune related receptors, such as for example Gp49, PIR, PIRA, PIRB, LIR, NKR-P1, NKp46, Digr1, ILT, MIR, KIR and the like. MHC may also include other classes such as MHC class II and MHC class III, derivatives and mutants thereof. The human MHC complex is also called the human leukocyte antigen (HLA) complex. MHC antigens are divided into MHC class I antigens (in humans, this class includes HLA-A, -B, and -C antigens) and MHC class II antigens (in humans, this class includes HLA-DP, -DQ, and -DR antigens). Thus, the terms "MHC-II antigens", "MHC class II antigens", and "MHC class II transplantation antigens" are used interchangeably herein to refer to the class of proteins, which in humans, includes HLA-DP, -DQ and -DR antigens. While the terms "MHC class II genes" and "MHC-II genes" are used interchangeably herein to refer to the genes which encode the MHC class II transplantation antigens. The term "MHC-II" is used herein to refer to the gene locus which encodes the MHC class II transplantation antigens, as well as the group of proteins encoded by that locus. Transplantation antigens also include cell surface molecules other than MHC class I and II antigens. These antigens include the following: (1) the ABO antigens involved in blood cell recognition; (2) cell adhesion molecules such as ICAM, which is involved in leukocyte cell-cell recognition; and (3) β2-microglobulin, a polypeptide associated with the 44 kd heavy chain polypeptide that comprises the HLA-I antigens but is not encoded by the MHC complex. HLA haplotypes/allotypes vary from individual to individual and it is often helpful to determine the individual's HLA type. The HLA type may be determined via standard typing procedures and the peripheral blood lymphocytes (PBLs) purified by Ficoll gradients.

The term "short-interfering RNAs (siRNA)" refers to small double-stranded RNAs that interfere with gene expression. siRNAs are an intermediate of RNA interference, the process by which double-stranded RNA silences homologous genes. siRNAs, are typically comprised of two single stranded RNAs, of about 21 nucleotides long that form a 19 base pair duplex with about 2 nucleotide 3' overhangs. Processing of the double stranded RNA by an enzymatic complex, for example polymerases, results in cleavage of the double stranded RNA to produce siRNAs. The antisense strand of the siRNA is used by an RNA interference (RNAi) silencing complex to guide mRNA cleavage, so promoting mRNA degradation. To silence a specific gene using siRNAs, for example in a mammalian cell, the base pairing region is selected to avoid chance complementarity to an unrelated mRNA. Sequence analysis programs, such as for example BLAST, can be conducted to determine the sequence of the desired gene target to be silenced. RNAi silencing complexes have been identified in the art. See for example, Fire, A. et al., 1998, *Nature,* 391:806-811 and McManus M T et al., *Nat. Rev. Genet.* 2002 October; 3(10):737-47.

As used herein, the term "interfering RNA (RNAi)" is double stranded RNA that results in catalytic degradation of specific mRNAs, and can also be used to lower gene expression. Natural nucleic acids have a phosphate backbone; artificial nucleic acids may contain other types of backbones, nucleotides, or bases. Artificial nucleic acids with modified backbones include peptide nucleic acids (PNAs), phosphothionates, phosphorothioates, phosphorodiamidate morpholino variants, and other variants of the phosphate backbone of native nucleic acids.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long.

As used herein, the term "specifically hybridizes" or "specifically detects" refers to the ability of a nucleic acid molecule to hybridize to at least approximately 6 consecutive nucleotides of a sample nucleic acid.

"Transcriptional regulatory sequence" is a generic term used throughout the specification to refer to DNA sequences, such as initiation signals, enhancers, promoters, silencing elements, which induce, inhibit or control transcription of protein coding sequences with which they are operably linked.

A "transgenic animal" refers to any animal, preferably a non-human mammal, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation; such as by microinjection or by infection with a recombinant virus. The term "genetic manipulation" does not include classical cross-breeding, or in vitro fertilization, but rather comprises the introduction of a recombinant DNA molecule. The heterologous molecule may be integrated within a chromosome, or it may be extrachromosomally replicating DNA. In a transgenic animal, the transgene causes cells to express a recombinant form of, for example, a class I MHC polypeptide. However, transgenic animals in which the recombinant gene is silent or deleted (knock-out mice) are also contemplated, as for example, the CD3z-/-; β2M-/-TAP1-/- and the like, mutant mice. Moreover, "transgenic animal" also includes those recombinant animals in which gene disruption of one or more genes is caused by human intervention, including both recombination and antisense techniques. The term is intended to include all progeny generations. Thus, the founder animal and all F1, F2, F3, and so on, progeny thereof are included.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

A vector is a composition which can transduce, transfect, transform or infect a cell, thereby causing the cell to express nucleic acids and/or proteins other than those native to the cell, or in a manner not native to the cell. A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell. A cell is "transformed" by a nucleic acid when the nucleic acid is transduced into the cell and stably replicated. A vector includes a nucleic acid (ordinarily RNA or DNA) to be expressed by the cell. A vector optionally includes materials to aid in achieving entry of the nucleic acid into the cell, such as a viral particle, liposome, protein coating or the like. A "cell transduction vector" is a vector which encodes a nucleic acid capable of stable replication and expression in a cell once the nucleic acid is transduced into the cell.

As used herein, a "target cell" or "recipient cell" refers to an individual cell or cell which is desired to be, or has been, a recipient of exogenous nucleic acid molecules, polynucleotides and/or proteins. The term is also intended to include progeny of a single cell.

"Label molecules" are chemical or biochemical moieties used for labeling a polynucleotide, a polypeptide, or an antibody. They include, but are not limited to, radionuclides, enzymes, substrates, cofactors, inhibitors, fluorescent agents, chromogenic agents, chemiluminescent agents, magnetic particles, and the like. Reporter molecules specifically bind, establish the presence of, and allow quantification of a particular polynucleotide, polypeptide, or antibody.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Substantially purified" refers to nucleic acid molecules or proteins that are removed from their natural environment and are isolated or separated, and are at least about 60% free, preferably about 75% free, and most preferably about 90% free, from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Neural defects, disorders or diseases" as used herein refers to any neurological disorder, including but not limited to neurodegenerative disorders (Parkinson's; Alzheimer's) or autoimmune disorders (multiple sclerosis) of the central nervous system; memory loss; long term and short term memory disorders; learning disorders; autism, depression, benign forgetfulness, childhood learning disorders, close head injury, and attention deficit disorder; autoimmune disorders of the brain, neuronal reaction to viral infection; brain damage; depression; psychiatric disorders such as bi-polarism, schizophrenia and the like; narcolepsy/sleep disorders (including circadian rhythm disorders, insomnia and narcolepsy); severance of nerves or nerve damage; severance of the cerebrospinal nerve cord (CNS) and any damage to brain or nerve cells; neurological deficits associated with AIDS; tics (e.g. Giles de la Tourette's syndrome); Huntington's chorea, schizophrenia, traumatic brain injury, tinnitus, neuralgia, especially trigeminal neuralgia, neuropathic pain, inappropriate neuronal activity resulting in neurodysthesias in diseases such as diabetes, MS and motor neurone disease, ataxias, muscular rigidity (spasticity) and temporomandibular joint dysfunction; Reward Deficiency Syndrome (RDS) behaviors in a subject.

As used herein, "RDS" behaviors are those behaviors that manifests as one or more behavioral disorders related to an individual's feeling of well-being with anxiety, anger or a craving for a substance. RDS behaviors include, alcoholism, SUD, smoking, BMI or obesity, pathological gambling, carbohydrate bingeing, axis 11 diagnosis, SAB, ADD/ADHD, CD, TS, family history of SUD, and Obesity. All these behaviors, and others described herein as associated with RDS behaviors or genes involved in the neurological pathways related to RDS, are included as RDS behaviors as part of this invention. Additionally, many of the clinical terms used herein for many specific disorders that are RDS disorders are found in the Quick Reference to the Diagnostic Criteria From DSM-IV™, The American Psychiatric Association, Washington, D.C., 1994.

Affective disorders, including major depression, and the bipolar, manic-depressive illness, are characterized by changes in mood as the primary clinical manifestation. Major depression is the most common of the significant mental illnesses, and it must be distinguished clinically from periods of normal grief, sadness and disappointment, and the related dysphoria or demoralization frequently associated with medical illness. Depression is characterized by feelings of intense sadness, and despair, mental slowing and loss of concentration, pessimistic worry, agitation, and self-deprecation. Physical changes can also occur, including insomnia, anorexia, and weight loss, decreased energy and libido, and disruption of hormonal circadian rhythms.

Mania, as well as depression, is characterized by changes in mood as the primary symptom. Either of these two extremes of mood may be accompanied by psychosis with disordered thought and delusional perceptions. Psychosis may have, as a secondary symptom, a change in mood, and it is this overlap with depression that causes much confusion in diagnosis. Severe mood changes without psychosis frequently occur in depression and are often accompanied by anxiety.

Parkinson's disease, independent of a specific etiology, is a chronic, progressive central nervous system disorder which usually appears insidiously in the latter decades of life. The disease produces a slowly increasing disability in purposeful movement. It is characterized by four major clinical features of tremor, bradykinesia, rigidity and a disturbance of posture. Often patients have an accompanying dementia. In idiopathic Parkinsonism, there is usually a loss of cells in the substantia nigra, locus ceruleus, and other pigmented neurons of the brain, and a decrease of dopamine content in nerve axon terminals of cells projecting from the substantia nigra. The understanding that Parkinsonism is a syndrome of dopamine deficiency and the discovery of levodopa as an important drug for the treatment of the disease were the logical culmination of a series of related basic and clinical observations, which serves as the rationale for drug treatment.

As used herein, the term "schizophrenia" refers to a psychiatric disorder that includes at least two of the following: delusions, hallucinations, disorganized speech, grossly disorganized or catatonic behavior, or negative symptoms. Patients can be diagnosed as schizophrenic using the DSM-IV criteria (APA, 1994, Diagnostic and Statistical Manual of Mental Disorders (Fourth Edition), Washington, D.C.).

The term "Alzheimer's Disease" refers to a progressive mental deterioration manifested by memory loss, confusion and disorientation beginning in late middle life and typically resulting in death in five to ten years. Pathologically, Alzheimer's Disease can be characterized by thickening, conglutination, and distortion of the intracellular neurofibrils, neurofibrillary tangles and senile plaques composed of granular or filamentous argentophilic masses with an amyloid core. Methods for diagnosing Alzheimer's Disease are known in the art. For example, the National Institute of Neurological and Communicative Disorders and Stroke-Alzheimer's Disease and the Alzheimer's Disease and Related Disorders Association (NINCDS-ADRDA) criteria can be used to diagnose Alzheimer's Disease (McKhann et al., 1984, Neurology 34:939-944). The patient's cognitive function can be assessed by the Alzheimer's Disease Assessment Scale-cognitive subscale (ADAS-cog; Rosen et al., 1984, Am. J. Psychiatry 141: 1356-1364).

As used herein, the term "autism" refers to a state of mental introversion characterized by morbid self-absorption, social failure, language delay, and stereotyped behavior. Patients can be diagnosed as suffering from autism by using the DSM-IV criteria.

As used herein, the term "depression" refers to a clinical syndrome that includes a persistent sad mood or loss of interest in activities, which lasts for at least two weeks in the absence of treatment. The DSM-IV criteria can be used to diagnose patients as suffering from depression.

The term "benign forgetfulness," as used herein, refers to a mild tendency to be unable to retrieve or recall information that was once registered, learned, and stored in memory (e.g., an inability to remember where one placed one's keys or parked one's car). Benign forgetfulness typically affects individuals after 40 years of age and can be recognized by standard assessment instruments such as the Wechsler Memory Scale (Russell, 1975, *J. Consult Clin. Psychol.* 43:800-809).

As used herein, the term "childhood learning disorders" refers to an impaired ability to learn, as experienced by certain children. Such learning disorders can be diagnosed by using the DSM-IV criteria.

The term "close head injury," as used herein, refers to a clinical condition after head injury or trauma which condition can be characterized by cognitive and memory impairment. Such a condition can be diagnosed as "amnestic disorder due to a general medical condition" according to DSM-IV.

The term "attention deficit disorder," as used herein, refers to a disorder that is most commonly exhibited by children and which can be characterized by increased motor activity and a decreased attention span. The DSM-IV criteria can be used to diagnose attention deficit disorder. Attention-deficit disorder ("ADD") is a common behavioral learning disorder in children which adversely affects school performance and family relationships. Symptoms and signs include hyperactivity (e.g., ADDH and AD/HD, DSM-IV), impulsivity, emotional lability, motor incoordination and some perceptual difficulties. Treatment has included psychostimulants, which while effective are controversial, and may cause troubling side effects such as dysphoria, headache and growth retardation. Other drugs, including the tricyclic antidepressants, appear to improve attention, but may be less effective than the psychostimulants.

"Diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein, a "pharmaceutically acceptable" component is one that is suitable for use with humans and/or animals without undue adverse side effects (such as toxicity, irritation, and allergic response) commensurate with a reasonable benefit/risk ratio.

The terms "patient" or "individual" are used interchangeably herein, and is meant a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

As used herein, "ameliorated" or "treatment" refers to a symptom which is approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests. For example, amelioration or treatment of depression includes, for example, relief from the symptoms of depression which include, but are not limited to changes in mood, feelings of intense sadness and despair, mental slowing, loss of concentration, pessimistic worry, agitation, and self-deprecation. Physical changes may also be relieved, including insomnia, anorexia and weight loss, decreased energy and libido, and the return of normal hormonal circadian rhythms. Another example, when using the terms "treating Parkinson's disease" or "ameliorating" as used herein means relief from the symptoms of Parkinson's disease which include, but are not limited to tremor, bradykinesia, rigidity, and a disturbance of posture.

"Cells of the immune system" or "immune cells" as used herein, is meant to include any cells of the immune system that may be assayed, including, but not limited to, B lymphocytes, also called B cells, T lymphocytes, also called T cells, natural killer (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types.

"Immune effector cells" refers to cells capable of binding an antigen and which mediate an immune response. These cells include, but are not limited to, T cells (T lymphocytes), B cells (B lymphocytes), monocytes, macrophages, natural killer (NK) cells and cytotoxic T lymphocytes (CTLs), for example CTL lines, CTL clones, and CTLs from tumor, inflammatory, or other infiltrates.

"Immune related molecules" refers to any molecule identified in any immune cell, whether in a resting ("non-stimulated") or activated state, and includes any receptor, ligand, cell surface molecules, nucleic acid molecules, polypeptides, variants and fragments thereof.

"T cells" or "T lymphocytes" are a subset of lymphocytes originating in the thymus and having heterodimeric receptors associated with proteins of the CD3 complex (e.g., a rearranged T cell receptor, the heterodimeric protein on the T cell surfaces responsible for antigen/MHC specificity of the cells). T cell responses may be detected by assays for their effects on other cells (e.g., target cell killing, macrophage, activation, B-cell activation) or for the cytokines they produce.

"CD4" is a cell surface protein important for recognition by the T cell receptor of antigenic peptides bound to MHC class II molecules on the surface of an APC. Upon activation, naïve CD4 T cells differentiate into one of at least two cell types, Th1 cells and TH2 cells, each type being characterized by the cytokines it produces. "Th1 cells" are primarily involved in activating macrophages with respect to cellular immunity and the inflammatory response, whereas "Th2 cells" or "helper T cells" are primarily involved in stimulating B cells to produce antibodies (humoral immunity). CD4 is the receptor for the human immunodeficiency virus (HIV). Effector molecules for Th1 cells include, but are not limited to, IFN-γ, GM-CSF, TNF-α, CD40 ligand, Fas ligand, IL-3, TNF-β, and IL-2. Effector molecules for Th2 cells include, but are not limited to, IL-4, IL-5, CD40 ligand, IL-3, GS-CSF, IL-10, TGF-β, and eotaxin. Activation of the Th1 type cytokine response can suppress the Th2 type cytokine response.

"CD8" is a cell surface protein important for recognition by the T cell receptor of antigenic peptides bound to MHC class I molecules. CD8 T cells usually become "cytotoxic T cells" or "killer T cells" and activate macrophages. Effector molecules include, but are not limited to, perforin, granzymes, Fas ligand, IFN-γ, TNF-α, and TNF-β.

"Activity", "activation" or "augmentation" is the ability of "resting" immune cells to respond and exhibit, on a measurable level, an immune function. Measuring the degree of activation refers to a quantitative assessment of the capacity of immune cells to express enhanced activity when further stimulated as a result of prior activation. The enhanced capacity may result from biochemical changes occurring during the activation process that allow the immune cells to be stimulated to activity in response to low doses of stimulants.

Immune cell activity that may be measured include, but is not limited to, (1) cell proliferation by measuring the cell or DNA replication; (2) enhanced cytokine production, including specific measurements for cytokines, such as IFN-γ, GM-CSF, or TNF-α; (3) cell mediated target killing or lysis; (4) cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; and, (9) apoptosis, which refers to fragmentation of activated immune cells under certain circumstances, as an indication of abnormal activation.

An "adjuvant" is any substance capable of enhancing the immune response to an antigen with which it is mixed. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol, as well as BCG (bacilli Calmette-Guerin) and *Corynabacterium parvum*, which are often used in humans, and ligands of CCR6 and other chemokine receptors.

A "chemokine" is a small cytokine involved in the migration and activation of cells, including phagocytes and lymphocytes, and plays a role in inflammatory responses.

A "cytokine" is a protein made by a cell that affect the behavior of other cells through a "cytokine receptor" on the surface of the cells the cytokine effects. Cytokines manufactured by lymphocytes are sometimes termed "lymphokines."

As used herein, the term "polypeptide" comprises amino acid chains of any length, including full length proteins comprising the sequences recited herein. A polypeptide comprising an epitope of a protein comprising a sequence as described herein may consist entirely of the epitope, or may contain additional sequences. The additional sequences may be derived from the native protein or may be heterologous, and such sequences may (but need not) possess immunogenic or antigenic properties.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein comprising epitope A (or free, unlabeled A) in a reaction comprising labeled "A" and the antibody will reduce the amount of labeled A bound to the antibody. "Specific binding" in general, refers to any immune related molecule binding to its ligand, such as for example the binding of a T cell receptor expressed by a T lymphocyte, to an MHC molecule and peptide on an antigen presenting cell.

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab)$_2$, and F(ab')$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

An "epitope", as used herein, is a portion of a polypeptide that is recognized (i.e., specifically bound) by a B-cell and/or T-cell surface antigen receptor. Epitopes may generally be identified using well known techniques, such as those summarized in Paul, Fundamental Immunology, 3rd ed., 243-247 (Raven Press, 1993) and references cited therein. Such techniques include screening polypeptides derived from the native polypeptide for the ability to react with antigen-specific antisera and/or T-cell lines or clones. An epitope of a polypeptide is a portion that reacts with such antisera and/or T-cells at a level that is similar to the reactivity of the full length polypeptide (e.g., in an ELISA and/or T-cell reactivity assay). Such screens may generally be performed using methods well known to those of ordinary skill in the art, such as those described in Harlow and Lane, Antibodies: A Laboratory Manual, Cold Spring Harbor Laboratory, 1988. B-cell and T-cell epitopes may also be predicted via computer analysis. Polypeptides comprising an epitope of a polypeptide that is preferentially expressed in a tumor tissue (with or without additional amino acid sequence) are within the scope of the present invention.

The terms "nucleic acid molecule" or "polynucleotide" will be used interchangeably throughout the specification, unless otherwise specified. As used herein, "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

As used herein, the term "fragment or segment", as applied to a nucleic acid sequence, gene or polypeptide, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid or peptide fragments which begin at the amino terminal end of a nucleic acid or protein and end at the carboxy terminal end of the nucleic acid or protein. Each nucleic acid or peptide fragment has at least about one contiguous nucleic acid or amino acid position in common with the next nucleic acid or peptide fragment, more preferably at least about three contiguous nucleic acid bases or amino acid positions in common, most preferably at least about ten contiguous nucleic acid bases amino acid positions in common.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides.

Homologous nucleic acid sequences, when compared, exhibit significant sequence identity or similarity. The standards for homology in nucleic acids are either measures for homology generally used in the art by sequence comparison or based upon hybridization conditions. The hybridization conditions are described in greater detail below.

As used herein, "substantial homology" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a fragment derived from a known immune related molecule, for example, a class I MHC molecule of known haplotype; Gp49, PIR, PIRA, PIRB, LIR, NKR-P1, NKp46, Digr1, ILT, MIR, KIR and the like. Typically, selective hybridization will occur when there is at least about 55% homology over a stretch of at least about 14 nucleotides, preferably at least about 65%, more preferably at least about 75%, and most preferably at least about 90%. See Kanehisa (1984) *Nuc. Acids Res.* 12:203-213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides. The endpoints of the segments may be at many different pair combinations.

The term "substantially purified", as used herein, refers to nucleic or amino acid sequences that are removed from their natural environment, isolated or separated, and are at least 60% free, preferably 75% free, and most preferably 90% free from other components with which they are naturally associated.

We have now shown that immune related molecules, such as for example, class I major histocompatibility complex (class I MHC) molecules, known to be important for immune responses to antigen, are expressed also by neurons that undergo activity-dependent, long-term structural and synaptic modifications. The invention provides that in mammals who are genetically deficient for cell surface class I MHC or for a class I MHC receptor component, namely CD3ζ, refinement of connections between retina and central targets during development is incomplete. In the hippocampus of adult mutants, N-methyl-D-aspartate receptor-dependent long-term potentiation (LTP) is enhanced, and long-term depression (LTD) is absent. Specific class I MHC messenger RNAs are expressed by distinct mosaics of neurons, reflecting a potential for diverse neuronal functions. These results demonstrate an important role for these molecules in the activity-dependent remodeling and plasticity of connections in the developing and mature mammalian central nervous system (CNS). Most importantly, the results of the invention show that brain wiring and cellular correlates of memory mechanisms are abnormal in mice lacking cell surface Class I MHC expression, or in knockout mice lacking CD3 zeta. CD3 zeta is a required component of the receptor system for Class I MHC in lymphocytes that we also found expressed in neurons. This discovery demonstrated a requirement for Class I MHC and a system of brain receptors for Class I in brain wiring and memory processes.

In a preferred embodiment, the invention provides screening methods (e.g., assays) for the identification of compounds which can be used to treat individuals suffering from immune related molecule mediated neuronal disorders. Immune related molecules include but not limited to Gp49, PIR, PIRA, PIRB, LIR, NKR-P1, NKp46, Digr1, ILT, MIR, KIR, class I MHC and the like and other immune-related receptors.

In another preferred embodiment, the invention provides for identification of molecules, such as for example, agonists and antagonists of the class I MHC and other immune-related receptor gene products, including small molecules, large molecules, and antibodies, as well as nucleotide sequences that can be used to inhibit Gp49, PIR, PIRA, PIRB, LIR, NKR-P1, NKp46, Digr1, ILT, MIR, KIR, class I MHC and other immune-related receptor gene expression (e.g., siRNA's, antisense and ribozyme molecules), and gene or regulatory sequence replacement constructs designed to enhance Gp49, PIR, PIRA, PIRB, LIR, NKR-P1, NKp46, Digr1, ILT, MIR, KIR, class I MHC and other immune-related receptor gene expression (e.g., expression constructs that place the class I MHC and other immune-related receptor gene under the control of a strong promoter system).

In accordance with the invention, cellular and non-cellular assays are described that can be used to identify compounds that interact with the Gp49, PIR, PIRA, PIRB, LIR, NKR-P1, NKp46, Digr1, ILT, MIR, KIR, class I MHC and other immune-related receptor gene products, e.g., modulate the activity of the class I MHC and other immune-related receptor and/or bind to the class I MHC and other immune-related receptor gene products. Such cell-based assays of the invention utilize cells, cell lines, or engineered cells or cell lines that express, for example, one or more molecules of Gp49, PIR, PIRA, PIRB, LIR, NKR-P1, NKp46, Digr1, ILT, MIR, KIR, class I MHC and other immune-related receptor gene product.

In particular, the present invention relates to the recognition of the functional association of, for example, Gp49, PIR, PIRA, PIRB, LIR, NKR-P1, NKp46, Digr1, ILT, MIR, KR, class I MHC with neuronal disorders, normal brain development and memory mechanisms. Class I MHC was identified using pan-specific MHC probes and was found to be expressed by neurons in specific patterns and at specific times throughout the brain. PIRB was also found, using a pan specific Pir probe, to be expressed in the brain. The PirB molecule was phosphorylated as determined by a standard phosphorylation assay.

The invention further relates to the identification of the CD3ζ gene expression in neuronal cells and its function in normal brain development and memory mechanisms.

In particular, the invention provides for methods for identifying drugs which inhibit, regulate or activate the interactions between the Class I MHC, the immune-related receptors and ligands thereof. This is useful in determining the therapeutic value of drugs and/or identification of novel drugs involved in neuronal disorders. For example: drugs for treating neurological diseases and disorders such as all agonists and antagonists that are known or designed to interact with Class I MHC and either the known receptors of Class I MHC or novel Class I MHC receptors present in neurons or the downstream signaling pathways; use of immunosuppressive drugs to the treatment of neurodegenerative disorders, (such as Parkinson's; Alzheimer's) or autoimmune disorders (multiple sclerosis) of the central nervous system.

The methods for identifying compounds capable of modulating the expression of the mammalian Gp49, PIR, PIRA, PIRB, LIR, NKR-P1, NKp46, Digr1, ILT, MIR, KIR, class I MHC and the immune-related gene receptors and/or the synthesis or activity of the mammalian such gene products, wherein such methods comprise contacting a compound with a cell that expresses, for example, a class I MHC gene, measuring the level of class I MHC gene expression, gene product expression or gene product activity, and comparing this level to the level of class I MHC gene expression, gene product expression, expression patterns thereof, or gene product activity produced by the cell in the absence of the compound, such that if the level obtained in the presence of the compound differs from that obtained in its absence, a compound capable of modulating the expression of the mammalian class I MHC gene and/or the synthesis or activity of the mammalian class I MHC gene products has been identified.

In accordance with the invention, drugs, which modulate the expression of immune related molecules can be used to for treatments for enhancing memory or reduce memory loss, especially in traumatized patients. Examples of such immune modulating drugs are, for example, cytokines known to induce Class I MHC expression in tissues, including neurons may also play a role in memory, autoimmune disorders of the brain, neuronal reaction to viral infection and narcolepsy/sleep disorders, immunophilins, FK506 and the like.

In another embodiment, methods of treatment of neurological disorders include: isolating, purifying, culturing neural stem cells and progenitor cells with appropriate drugs and screening of the neural cells for the desired expression patterns of, for example, Gp49, PIR, PIRA, PIRB, LIR, NKR-P1, NKp46, Digr1, ILT, MIR, KIR, class I MHC and other immune-related receptors prior to transplantation into patients. Preferred cells within a stem cell population of the present invention include cells of at least one of the following cellular lineages: hematopoietic cell lineage, endothelial cell lineage, epithelial cell lineage, muscle cell lineage and neural cell lineage. Other preferred cells within a stem cell population of the present invention include cells of erythroid lineage, endothelial lineage, leukocyte lineage, thrombocyte lineage, erythroid lineage (including primitive and definitive erythroid lineages), macrophage lineage, neutrophil lineage, mast cell lineage, megakaryocyte lineage, natural killer cell lineage, eosinophil lineage, T cell lineage, endothelial cell lineage and B cell lineage. Most preferred are the neural and immune cell lineage such as T-, NK-, B-cell lineages.

The terms, "progenitor cell" will be used interchangeably with "precursor cell" and can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of neuronal lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). For example, a pluripotent cell can differ from a totipotent cell by having the ability to develop into all cell lineages except endothelial cells. A "pluripotent population of cells" refers to a composition of cells capable of developing into less than all lineages of cells but at least into all hematopoietic lineages. As such, a totipotent cell or composition of cells is less developed than a pluripotent cell or compositions of cells. As used herein, the terms "develop", "differentiate" and "mature" all refer to the progression of a cell from the stage of having the potential to differentiate into at least two different cellular lineages to becoming a specialized cell. Such terms can be used interchangeably for the purposes of the present application.

As used herein, the term "population" refers to cells having the same or different identifying characteristics. The term "lineage" refers to all of the stages of the development of a cell type, from the earliest precursor cell to a completely mature cell (i.e. a specialized cell such as a neuronal cell).

The invention further comprises methods for the treatment of mammalian immune related molecule mediated neuropsychiatric and other neuronal disorders resulting from, for example, abnormal MHC and other immune related receptor expression, wherein such methods comprise supplying the mammal with a nucleic acid molecule encoding normal gene products such that unimpaired MHC or other immune related receptors are expressed and symptoms of the disorder are ameliorated.

The invention further comprises methods for the treatment of mammalian MHC mediated neuropsychiatric and other neuronal disorders resulting from abnormal MHC and other immune related receptor gene mutations, wherein such methods comprise supplying the mammal with a cell comprising a nucleic acid molecule that encodes an unimpaired MHC or other immune related receptor gene products such that the cell expresses the unimpaired MHC or other immune related receptor gene products and symptoms of the disorder are ameliorated.

In addition, the present invention comprises methods that utilize the MHC or other immune related receptors gene and/or gene product sequences for the diagnostic evaluation, genetic testing and prognosis of a Class I MHC-mediated neuronal disorder. For example, the invention relates methods for diagnosing disorders wherein neuronal cells have abnormal pattern expressions or lack expression of class I MHC or other immune related receptors. Such methods comprise measuring the above gene expression in a patient sample, or detecting an MHC mutation in the genome of the mammal suspected of exhibiting such a disorder.

The invention also includes the discovery that part of the T-cell receptor (TCR) beta locus is expressed by neurons of the mammalian CNS in vivo, using in situ hybridization methods with probes specific for the two TCR beta constant regions. Surprisingly, TCR is expressed by neurons in olfactory bulb, thalamus, hypothalamus, and cortex of newborn mice. Unspliced T-cell receptor genes were also found to be present in neurons.

The invention also comprises the identification of the presence of mRNA for several activating and inhibitory receptors; and receptor systems, such as for example, Gp49, PIR, PIRA, PIRB, LIR, NKR-P1, NKp46, Digr1, ILT, MIR, KIR, class I MHC, used by lymphocytes and other immune cells. In the immune system, similar receptors can either bind class I MHC directly or alter class I MHC signaling mechanisms. The identified immune-related receptors include, but are not limited to Gp49, PIR, PIRA, PIRB, LIR, NKR-P1, NKp46, Digr1, ILT, MIR, KIR, class I MHC.

In accordance with the invention, other related receptors are contemplated. For example, Ig superfamily members.

Neuron-neuron interactions mediated by Ig family adhesion molecules are important in the establishment of brain architecture, in most cases via their effects on neuronal adhesion and synaptic strength, and MHCI is a founding member of the Ig superfamily. Many additional Ig-comprising molecules are central to MHCI signaling in the immune system, including class I MHC (MHCI) receptor components, adhesion molecules, and costimulatory receptors and their ligands. These Ig family proteins, like, for example, MHCI, may modulate neuronal adhesion and changes in synaptic strength in neurons.

Other examples include, but not limited to:

Cadherins

Cadherins are Ig family members that perform multiple functions in the brain through homophilic cell-cell adhesion. In *Drosophila melanogaster*, N-cadherin has been implicated in the targeting of connections made by developing photoreceptor neurons. Cadherin receptors are localized to synapses and associate with Fyn, suggesting a potential role for cadherin signaling in synaptic function and/or plasticity. Candidate Cadherins are expressed on T lymphocytes, where they may participate in cell recognition and adhesion.

Thy-1

Thy-1, another member of the Ig superfamily, regulates T cell signaling, likely via its interaction with other cell surface molecules on antigen-presenting cells. Although it was first described on mouse thymocytes, Thy-1 is one of the most abundant glycoproteins on mammalian neurons, where it is enriched at synapses and is involved in adhesion. The developmental appearance of Thy-1 in mouse brain closely parallels the histological and physiological maturation of neurons, with highest expression during the peak of activity-dependent rearrangements, during early postnatal life. Thy-1 is required for LTP, a process thought to underlie learning and memory, in specific regions of mammalian hippocampus, and antibodies against Thy-1 abolish long-term memory in chicks. Thy-1 is expressed on almost all neurons after the completion of axonal growth, and introduction of Thy-1 into a neuronal cell line inhibits neurite outgrowth in vitro. The presence of Thy-1 in retinal projections during retinal afferent segregation, without wishing to be bound by theory, raises the possibility that MHCI could restrict retinal axons to eye-specific layers through Thy-1-mediated inhibition of axonal extension.

Specific Phosphatases and Kinases

Src Protein Tyrosine Kinases

Fyn is a member of the Src family of kinases that is activated by the TCR-CD3 complex and transduces early events in T cell signaling. Fyn is also expressed in neural growth cones and axons, and Fyn-deficient mice exhibit reduced neurite outgrowth in response to neural cell adhesion molecule in vitro. Hippocampal LTP is impaired in Fyn knockout mice, and can be rescued by restoring Fyn in the hippocampus via a transgene under the CamKII promoter.

Calcineurin

Calcineurin is a calcium/calmodulin-dependent serine/threonine phosphatase that is activated by sustained low-level $Ca^{2+}$ signals arising during TCR signaling. Calcineurin is required for the induction of cytokine expression and T cell proliferation. In the brain, calcineurin is thought to be important in limiting LTP and may be required for LTD. Without wishing to be bound by theory, these effects may in part be due to calcineurin's ability to induce desensitization of N-methyl D-aspartate (NMDA) receptors during synaptic stimulation. Inhibiting the function of calcineurin enhances LTP and may prevent LTD, as does the lack of MHCI signaling.

The Calcineurin inhibitors cyclosporin A and FK506 are used clinically in the treatment of patients undergoing organ transplantation, where they are effective in preventing host-graft rejection. Because receptors for these drugs (immunophilins) are far more abundant in the nervous system than in the immune system, FK506 and cyclosporin A could have serious side-effects in the CNS. Indeed, adverse neuronal effects of immunosuppressive therapies have been reported, including headaches, tremor, neurotoxicity, hallucinations, seizures, and coma. However, lower doses of these Calcineurin inhibitors may be effective immunosuppressants without appreciable neurologic effects, illustrating the clinical importance of further study of conserved signaling mechanisms between the immune and central nervous systems.

ERK and JNK

Extracellular signal-regulated kinase (ERK) and c-Jun $NH_2$-terminal kinase (JNK) are mitogen-activated protein kinases that are crucial for development, activation, and differentiation of T cells. These kinase cascades mediate cytokine and growth factor signals, affecting the growth and survival of thymocytes as well as neurons. ERKs and JNKs have also been implicated in many activity-dependent neuronal events including LTP and LTD.

Adapter Proteins

Immune adapter proteins do not have enzymatic or transcriptional activity themselves, but rather participate in complexes that regulate such activity. Adapter proteins couple antigen receptor ligation to functional responses in lymphocytes, and are crucial for the formation of effective signaling complexes in the immune system.

Post-Translational Regulation

Neuronal activity may also regulate MHCI function post-translationally. In the immune system; depolarization of non-neuronal antigen-presenting cells causes a rapid, reversible conformational change in MHCI that is thought to affect its recognition by receptors. Indeed, changes in the membrane potential of MHCI-expressing nonneuronal target cells can enhance TCR signaling. There is also evidence that depolarization of the T cells themselves inhibits T cell signaling. In these experiments, pharmacologic blockade of voltage-dependent and $Ca^{2+}$-activated $K^+$ channels resulted in membrane depolarization and subsequent inhibition of T-cell activation. T cell signaling is also inhibited by activation of endogenous $GABA_A$ receptors, which are likely to be depolarizing, as the resting membrane potential is more negative than the $Cl^-$ equilibrium potential in T cells. Thus, depolarization of neurons expressing either MHCI or MHCI receptors may rapidly regulate the efficiency of MHCI-receptor interactions and downstream signaling.

Without wishing to be bound by theory, it is likely that these signaling molecules, if they are activated downstream of MHCI-receptor binding in neurons lead to a distinct, neuron-specific readout in the CNS. Consistent with this possibility, replacement of the TCR with a muscarinic acetylcholine receptor harnesses the downstream machinery of the T cell in response to muscarinic receptor activation. Similarly, the activation of mediators of MHCI function in neurons may lead to the forms of neuronal plasticity with which they are associated in neurons. For example, activation of calcineurin downstream of MHCI in neurons might lead to LTD, in neurons, rather than proliferation, as it is known to in T cells.

The invention also comprises the use of cell-based assays or cell-lysate assays (e.g., in vitro transcription or translation assays) to screen for compounds or compositions that modulate immunoreceptor gene expression. To this end, constructs comprising a reporter sequence linked to a regulatory element of the immunoreceptor gene can be used in engineered cells, or in cell lysate extracts, to screen for compounds that modulate the expression of the reporter gene product at the level of transcription. For example, such assays could be used to identify compounds that modulate the expression or activity of transcription factors involved in immunoreceptor gene expression, or to test the activity of triple helix polynucleotides. Alternatively, engineered cells or translation extracts can be used to screen for compounds (including antisense and ribozyme constructs) that modulate the translation of immunoreceptor mRNA transcripts, and therefore, affect expression of the immunoreceptor gene product.

The invention also comprises immunoreceptor gene products, polypeptides (including soluble immunoreceptor polypeptides or peptides) and immunoreceptor fusion proteins for use in non-cell based screening assays, for use in generating antibodies, for diagnostics and therapeutics. Such peptides or polypeptides can be fused to a heterologous protein, e.g., reporter, an Ig Fc region, etc., to yield a fusion protein. Such peptides, polypeptides and fusion proteins can be used in the non-cell based assays for screening compounds that interact with, e.g., modulate the activity of the immunoreceptor gene product and/or bind to the immunoreceptor gene product.

Immunoreceptor proteins can be used to treat neuropsychiatric and other neurological disorders, such as abnormal neural development, abnormal structural and synaptic functioning and neural plasticity. Such immunoreceptor gene products include but are not limited to soluble derivatives such as peptides or polypeptides corresponding to one or more domains of the immunoreceptor gene product. Alternatively, antibodies to the immunoreceptor protein or anti-idiotypic antibodies that mimic the immunoreceptor gene product (including Fab fragments), antagonists or agonists can be used to treat neuronal disorders involving immunoreceptor. In yet another approach, nucleotide constructs encoding such immunoreceptor gene products can be used to genetically engineer host cells to express such immunoreceptor gene products for transplantation in vivo.

In addition, this invention presents methods for the diagnostic evaluation and prognosis of neuronal and neuropsychiatric disorders, such as Alzheimer's and Parkinson's' disease. For example, nucleic acid molecules encoding immunoreceptors can be used as diagnostic hybridization probes or as primers for diagnostic PCR analysis for the identification of immunoreceptor gene mutations, allelic variations and regulatory defects in the immunoreceptor gene.

"Gene therapy" approaches for the modulation of immunoreceptor gene expression and/or activity in the treatment of neuronal disorders are within the scope of the invention. For example, nucleotide constructs encoding functional immunoreceptor gene, mutant immunoreceptor gene, as well as siRNAs, antisense and ribozyme molecules can be used to modulate immunoreceptor gene expression.

The invention also comprises pharmaceutical formulations and methods for treating brain and CNS disorders involving the immunoreceptor gene. The present invention presents methods for selecting an effective drug to administer to an individual having an immunoreceptor medicated disorder. Such methods can be based on the detection of genetic polymorphisms in the immunoreceptor gene or variations in immunoreceptor gene expression and patterns of expression, or lack thereof, due to altered methylation, differential spinning, or post-transductional modification of the immunoreceptor gene product which can affect the safety and efficacy of a therapeutic agent.

Identification of Immune Related Nucleic Acid Sequences in Neuronal Cells.

With respect to the cloning of allelic variants of the human immunoreceptor gene and homologues from other species (e.g., mouse), isolated immunoreceptor gene sequences may be labeled and used to screen a cDNA library constructed from mRNA obtained from appropriate cells or tissues (e.g., brain tissues) derived from the organism (e.g., mouse) of interest. The hybridization conditions used should be of a lower stringency when the cDNA library is derived from an organism different from the type of organism from which the labeled sequence was derived.

Alternatively, the labeled fragment may be used to screen a genomic library derived from the organism of interest, again, using appropriately stringent conditions. Low stringency conditions are well known to those of skill in the art, and will vary predictably depending on the specific organisms from which the library and the labeled sequences are derived. For guidance regarding such conditions see, for example, Sambrook, et al., 1989, Molecular Cloning, A Laboratory Manual, Second Edition, Cold Spring Harbor Press, N.Y.; and Ausubel, et al., 1989, Current Protocols in Molecular Biology, Green Publishing Associates and Wiley Interscience, N.Y.

Further, an immunoreceptor gene allelic variant may be isolated from, for example, human nucleic acid, by performing PCR using the pan specific probes as described in detail in the Examples section, e.g. Pan PIRB probe. For example, the template for the reaction may be cDNA obtained by reverse transcription of mRNA prepared from, for example, human or non-human cell lines or tissue known or suspected to express a PIR gene or allelic variant thereof. Preferably, the allelic variant will be isolated from an individual who has a PIR mediated neuronal disorder. This method is also used to determine the absence of any immunoreceptor expression.

PCR technology may also be utilized to isolate full length cDNA sequences. For example, RNA may be isolated, following standard procedures, from an appropriate cellular or tissue source (i.e., one known, or suspected, to express the immunoreceptor gene, such as, for example, brain tissue samples obtained through biopsy or post-mortem). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAse H, and second strand synthesis may then be primed with a poly-C primer. Thus, cDNA sequences upstream of the amplified fragment may easily be isolated. For a review of cloning strategies that may be used, see e.g., Sambrook et al., 1989, infra.

Another preferred method includes SAGE. Serial Analysis of Gene Expression (SAGE), is based on the identification of and characterization of partial, defined sequences of transcripts corresponding to gene segments. These defined transcript sequence "tags" are markers for genes which are expressed in a cell, a tissue, or an extract, for example.

SAGE is based on several principles. First, a short nucleotide sequence tag (9 to 10 bp) contains sufficient information content to uniquely identify a transcript provided it is isolated from a defined position within the transcript. For example, a sequence as short as 9 bp can distinguish about 262,144 transcripts given a random nucleotide distribution at the tag site, whereas estimates suggest that the human genome encodes about 80,000 to 200,000 transcripts (Fields, et al., *Nature Genetics,* 7:345 1994). The size of the tag can be shorter for lower eukaryotes or prokaryotes, for example, where the number of transcripts encoded by the genome is lower. For example, a tag as short as 6-7 bp may be sufficient for distinguishing transcripts in yeast.

Second, random dimerization of tags allows a procedure for reducing bias (caused by amplification and/or cloning). Third, concatenation of these short sequence tags allows the efficient analysis of transcripts in a serial manner by sequencing multiple tags within a single vector or clone. As with serial communication by computers, wherein information is transmitted as a continuous string of data, serial analysis of the sequence tags requires a means to establish the register and boundaries of each tag. The concept of deriving a defined tag from a sequence in accordance with the present invention is useful in matching tags of samples to a sequence database. In the preferred embodiment, a computer method is used to match a sample sequence with known sequences.

The tags used herein, uniquely identify genes. This is due to their length, and their specific location (3') in a gene from which they are drawn. The full length genes can be identified by matching the tag to a gene data base member, or by using the tag sequences as probes to physically isolate previously unidentified genes from cDNA libraries. The methods by which genes are isolated from libraries using DNA probes are well known in the art. See, for example, Veculescu et al., *Science* 270: 484 (1995), and Sambrook et al. (1989), MOLECULAR CLONING: A LABORATORY MANUAL, 2nd ed. (Cold Spring Harbor Press, Cold Spring Harbor, N.Y.). Once a gene or transcript has been identified, either by matching to a data base entry, or by physically hybridizing to a cDNA molecule, the position of the hybridizing or matching region in the transcript can be determined. If the tag sequence is not in the 3' end, immediately adjacent to the restriction enzyme used to generate the SAGE tags, then a spurious match may have been made. Confirmation of the identity of a SAGE tag can be made by comparing transcription levels of the tag to that of the identified gene in certain cell types.

Analysis of gene expression is not limited to the above method but can include any method known in the art. All of these principles may be applied independently, in combination, or in combination with other known methods of sequence identification.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (reviewed in (To, Comb. Chem. High Throughput Screen, 2000, 3, 235-41).

In a preferred embodiment, Expressed Sequenced Tags (ESTs), can also be used to identify nucleic acid molecules which are over expressed in a neuronal cell. ESTs from a variety of databases can be indentified. For example, preferred databases include, for example, Online Mendelian Inheritance in Man (OMIM), the Cancer Genome Anatomy Project (CGAP), GenBank, EMBL, PIR, SWISS-PROT, and the like. OMIM, which is a database of genetic mutations associated with disease, was developed, in part, for the National Center for Biotechnology Information (NCBI). OMIM can be accessed through the world wide web of the Internet, at, for example, ncbi.nlm.nih.gov/Omim/. CGAP, which is an interdisciplinary program to establish the information and technological tools required to decipher the molecular anatomy of a cancer cell. CGAP can be accessed through the world wide web of the Internet, at, for example, ncbi.nlm.nih.gov/ncicgap/. Some of these databases may contain complete or partial nucleotide sequences. In addition, alternative transcript forms can also be selected from private genetic databases. Alternatively, nucleic acid molecules can be selected from available publications or can be determined especially for use in connection with the present invention.

Alternative transcript forms can be generated from individual ESTs which are within each of the databases by computer software which generates contiguous sequences. In another embodiment of the present invention, the nucleotide sequence of the nucleic acid molecule is determined by assembling a plurality of overlapping ESTs. The EST database (dbEST), which is known and available to those skilled in the art, comprises approximately one million different human mRNA sequences comprising from about 500 to 1000 nucleotides, and various numbers of ESTs from a number of different organisms. dbEST can be accessed through the world wide web of the Internet, at, for example, ncbi.nlm.nih.gov/dbEST/index.html. These sequences are derived from a cloning strategy that uses cDNA expression clones for genome sequencing. ESTs have applications in the discovery of new genes, mapping of genomes, and identification of coding regions in genomic sequences. Another important feature of EST sequence information that is becoming rapidly available is tissue-specific gene expression data. This can be extremely useful in targeting selective gene(s) for therapeutic intervention. Since EST sequences are relatively short, they must be assembled in order to provide a complete sequence. Because every available clone is sequenced, it results in a number of overlapping regions being reported in the database. The end result is the elicitation of alternative transcript forms from, for example, immune cells and neuronal cells.

Assembly of overlapping ESTs extended along both the 5' and 3' directions results in a full-length "virtual transcript." The resultant virtual transcript may represent an already characterized nucleic acid or may be a novel nucleic acid with no known biological function. The Institute for Genomic Research (TIGR) Human Genome Index (HGI) database, which is known and available to those skilled in the art, contains a list of human transcripts. TIGR can be accessed through the world wide web of the Internet, at, for example, tigr.org. Transcripts can be generated in this manner using TIGR-Assembler, an engine to build virtual transcripts and which is known and available to those skilled in the art. TIGR-Assembler is a tool for assembling large sets of overlapping sequence data such as ESTs, BACs, or small genomes, and can be used to assemble eukaryotic or prokaryotic sequences. TIGR-Assembler is described in, for example, Sutton, et al., *Genome Science & Tech.*, 1995, 1, 9-19, which is incorporated herein by reference in its entirety, and can be accessed through the file transfer program of the Internet, at, for example, tigr.org/pub/software/TIGR. assembler. In addition, GLAXO-MRC, which is known and available to those skilled in the art, is another protocol for constructing virtual transcripts. PHRAP is used for sequence assembly within Find Neighbors and Assemble EST Blast. PHRAP can be accessed through the world wide web of the Internet, at, for example, chimera.biotech.washington.edu/uwgc/tools/phrap.htm. Identification of ESTs and generation of contiguous ESTs to form full length RNA molecules is described in detail in U.S. application Ser. No. 09/076,440, which is incorporated herein by reference in its entirety.
Identification of Immune-Related Molecules Expressed in Neural Disorders.

As mentioned above, the immunoreceptor gene sequences may be used to isolate mutant immunoreceptor gene alleles, preferably from a human subject. Such mutant alleles may be isolated from individuals either known or proposed to have a genotype that contributes to the symptoms of a neuronal disorder such as Alzheimer's or Parkinson's disease.

A cDNA of a mutant allelic variant of the immunoreceptor gene may be isolated, for example, by using PCR, a technique that is well known to those of skill in the art. In this case, the first cDNA strand may be synthesized by hybridizing an oligo-dT oligonucleotide to mRNA isolated from tissue known or suspected to be expressed in an individual putatively carrying the mutant immunoreceptor allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant immunoreceptor allele to that of the normal immunoreceptor allele, the mutation(s) responsible for the loss or alteration of function of the mutant immunoreceptor gene product can be ascertained. Furthermore, expression levels and expression patterns of class I MHC or other receptors can be determined as described more fully in the examples which follow.

Genomic DNA isolated from lymphocytes or other immune cells of normal and affected individuals can also be used as PCR template. PCR products from normal and affected individuals are compared, either by single strand conformational polymorphism (SSCP) mutation detection techniques and/or by sequencing. The mutations responsible for the loss or alteration of function of the neural class I MHC or other immunoreceptor gene product can then be ascertained.

In another embodiment of the invention, the above nucleic acid sequences encoding immunoreceptors may be used to generate hybridization probes useful in mapping the naturally-occurring genomic sequence, as well as to detect in an individual, or group of individuals, allelic variants of genes that are present in individuals suffering from or susceptible to neural defects or diseases. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries (see, e.g., Harrington et al., 1997, *Nat. Genet.* 15: 345-355; Price, 1993, *Blood Rev.* 7: 127-134; and Trask, 1991, *Trends Genet.* 7: 149-154).

Fluorescent in situ hybridization (FISH) may be correlated with other physical chromosome mapping techniques and genetic map data (see, e.g., Heinz-Ulrich et al., 1995, in Meyers, supra, pp. 965-968). Examples of genetic map data can be found in various scientific journals or at the Online Mendelian Inheritance in Man (OMIM) site. Correlation between the location of the gene encoding for example, Digr1, on a physical chromosomal map and a neural disease or defect, may help define the region of DNA associated with such abnormalities. The nucleotide sequences of the invention may be used to detect differences in gene sequences among resistant, susceptible, or allelic variants in individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for genes of the invention using positional cloning or other gene discovery techniques. Once the genes have been crudely localized by genetic linkage to a particular genomic region, e.g., ataxia-telangiectasia to 11q22-23, any sequences mapping to that area may represent associated or regulatory genes for further investigation (see, e.g., Gatti et al., 1988, *Nature* 336:577-580). Other examples of particular genomic regions include, but not limited to, leukocyte receptor cluster to 19q13.3-13.4 The nucleotide sequence of the subject invention may also be used to detect differences in the chromosomal location due to translocation, inversion, etc., among normal, or affected individuals.

The genes identified from individuals are amplified by PCR and sequenced by methods well known in the art. These nucleic acid sequences are then used in the assays described in the examples and materials and methods to correlate the sequence of the genes identified, with, for example, the percentage of individuals suffering from Alzheimer's disease as compared to normal individuals. As more gene sequences and their amino acid sequences are identified, allows for a correlation between the expression of immunoreceptors in cells of the nervous system, including the brain, and individuals predisposed to a neural disease or defect.

In yet another aspect, variants of the nucleic acid molecules as identified in immune cells from individuals of different haplotypes and/or suffering from or susceptible to neural defects can be used to detect allelic variations of immune related molecules in neural cells. An "allele" or "variant" is an alternative form of a gene. Of particular utility in the invention are variants of the genes encoding any potential immune related molecule in the nervous system identified by the methods of this invention. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides: Each of these types of changes may occur alone, or in combination with the others, one or more times in a given sequence.

To further identify variant nucleic acid molecules which can detect, for example, early stage Alzheimer's, nucleic acid molecules can be grouped into sets depending on the homology, for example. The members of a set of nucleic acid molecules are compared. Preferably, the set of nucleic acid molecules is a set of alternative transcript forms of nucleic acid. Preferably, the members of the set of alternative transcript forms of nucleic acids include at least one member which is associated, or whose encoded protein is associated, with a disease state or biological condition. For example, a set of immune related molecules from immune cells and neural cells from normal and a diseased individual are compared. At least one of the members of the set of nucleic acid molecule alternative transcript forms can be associated with for example, Alzheimer's or any other neural defect, as described above. Thus, comparison of the members of the set of nucleic acid molecules results in the identification of at least one alternative transcript form of nucleic acid molecule which is associated, or whose encoded protein is associated, with a disease state or biological condition. In a preferred embodiment of the invention, the members of the set of nucleic acid molecules are from a common gene. In another embodiment of the invention, the members of the set of nucleic acid molecules are from a plurality of genes. In another embodiment of the invention, the members of the set of nucleic acid molecules are from different taxonomic species. Nucleotide sequences of a plurality of nucleic acids from different taxonomic species can be identified by performing a sequence similarity search, an ortholog search, or both, such searches being known to persons of ordinary skill in the art.

Sequence similarity searches can be performed manually or by using several available computer programs known to those skilled in the art. Preferably, Blast and Smith-Waterman algorithms, which are available and known to those skilled in the art, and the like can be used. Blast is NCBI's sequence similarity search tool designed to support analysis of nucleotide and protein sequence databases. Blast can be accessed through the world wide web of the Internet, at, for example, ncbi.nlm.nih.gov/BLAST/. The GCG Package provides a local version of Blast that can be used either with public domain databases or with any locally available searchable database. GCG Package v9.0 is a commercially available software package that contains over 100 interrelated software programs that enables analysis of sequences by editing, mapping, comparing and aligning them. Other programs included in the GCG Package include, for example, programs which facilitate RNA secondary structure predictions, nucleic acid fragment assembly, and evolutionary analysis. In addition, the most prominent genetic databases (GenBank, EMBL, PIR, and SWISS-PROT) are distributed along with the GCG Package and are fully accessible with the database searching and manipulation programs. GCG can be accessed through the Internet at, for example, http://www.gcg.com/. Fetch is a tool available in GCG that can get annotated GenBank records based on accession numbers and is similar to Entrez. Another sequence similarity search can be performed with GeneWorld and GeneThesaurus from Pangea. GeneWorld 2.5 is an automated, flexible, high-throughput application for analysis of polynucleotide and protein sequences. GeneWorld allows for automatic analysis and annotations of sequences. Like GCG, GeneWorld incorporates several tools for homology searching, gene finding, multiple sequence alignment, secondary structure prediction, and motif identification. GeneThesaurus 1.0™ is a sequence and annotation data subscription service providing information from multiple sources, providing a relational data model for public and local data.

Another alternative sequence similarity search can be performed, for example, by BlastParse. BlastParse is a PERL script running on a UNIX platform that automates the strategy described above. BlastParse takes a list of target accession numbers of interest and parses all the GenBank fields into "tab-delimited" text that can then be saved in a "relational database" format for easier search and analysis, which provides flexibility. The end result is a series of completely parsed GenBank records that can be easily sorted, filtered, and queried against, as well as an annotations-relational database.

Preferably, the plurality of nucleic acids from different taxonomic species which have homology to the target nucleic acid, as described above in the sequence similarity search, are further delineated so as to find orthologs of the target nucleic acid therein. An ortholog is a term defined in gene classification to refer to two genes in widely divergent organisms that have sequence similarity, and perform similar functions within the context of the organism. In contrast, paralogs are genes within a species that occur due to gene duplication, but have evolved new functions, and are also referred to as isotypes. Optionally, paralog searches can also be performed. By performing an ortholog search, an exhaustive list of homologous sequences from as diverse organisms as possible is obtained. Subsequently, these sequences are analyzed to select the best representative sequence that fits the criteria for being an ortholog. An ortholog search can be performed by programs available to those skilled in the art including, for example, Compare. Preferably, an ortholog search is performed with access to complete and parsed GenBank annotations for each of the sequences. Currently, the records obtained from GenBank are "flat-files", and are not ideally suited for automated analysis. Preferably, the ortholog search is performed using a Q-Compare program. Preferred steps of the Q-Compare protocol are described in the flowchart set forth in U.S. Pat. No. 6,221,587, incorporated herein by reference.

Preferably, interspecies sequence comparison is performed using Compare, which is available and known to those skilled in the art. Compare is a GCG tool that allows pair-wise comparisons of sequences using a window/stringency criterion. Compare produces an output file comprising points where matches of specified quality are found. These can be plotted with another GCG tool, DotPlot.

The polynucleotides of this invention can be isolated using the technique described in the experimental section or replicated using PCR. The PCR technology is the subject matter of U.S. Pat. Nos. 4,683,195, 4,800,159, 4,754,065, and 4,683,202 and described in PCR: The Polymerase Chain Reaction (Mullis et al. eds, Birkhauser Press, Boston (1994)) or MacPherson et al. (1991) and (1994), supra, and references cited therein. Alternatively, one of skill in the art can use the sequences provided herein and a commercial DNA synthesizer to replicate the DNA. Accordingly, this invention also provides a process for obtaining the polynucleotides of this invention by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the polynucleotide into a suitable replication vector and insert the vector into a suitable host cell (procaryotic or eucaryotic) for replication and amplification. The DNA so amplified can be isolated from the cell by methods well known to those of skill in the art. A process for obtaining polynucleotides by this method is further provided herein as well as the polynucleotides so obtained.

In an embodiment of the invention the presence of the one or more immune related nucleic acid molecules, isolated from an immune cell, is correlated to neuronal cell sample of a normal subject and one suffering from or susceptible to a neural disorder. The sample is preferably obtained from a mammal suspected of having a nerve or brain cell disorder. Preferably, a nucleic acid molecule that is indicative of an immune related molecule and detected in a neural cell comprises a sequence having at least about 80% sequence identity to a desired immune related molecule, such as for example class I MHC of known haplotype, more preferably the nucleic acid molecule comprises a sequence having at least about 90% sequence identity to a desired immune related molecule, such as for example class I MHC of known haplotype, most preferably the nucleic acid molecule comprises a sequence having at least about 95% sequence identity to a desired immune related molecule, such as for example class I MHC of known haplotype.

In another preferred embodiment of the invention the presence of the one or more immune related nucleic acid molecules, isolated from an immune cell, is correlated to neuronal cell sample of a normal subject and one suffering from or susceptible to a neural disorder. The sample is preferably obtained from a mammal suspected of having a nerve or brain cell disorder. Preferably, a nucleic acid molecule that is indicative of an immune related molecule and detected in a neural cell comprises a sequence having at least about 80% sequence identity to a desired immune related molecule, such as for example PIRB, more preferably the nucleic acid molecule comprises a sequence having at least about 90% sequence identity to a desired immune related molecule, such as for example PIRB, most preferably the nucleic acid molecule comprises a sequence having at least about 95% sequence identity to a desired immune related molecule, such as for example PIRB.

Preferably, a nucleic acid molecule that is indicative of an immune related molecule and detected in a neural cell comprises a sequence having at least about 80% sequence identity to a desired immune related molecule, such as for example Gp49, PIR, PIRA, PIRB, LIR, NKR-P1, NKp46, Digr1, ILT, MIR, KIR, class I MHC, more preferably the nucleic acid molecule comprises a sequence having at least about 90% sequence identity to a desired immune related molecule, such as for example Gp49, PIR, PIRA, PIRB, LIR, NKR-P1, NKp46, Digr1, ILT, MIR, KIR, class I MHC, most preferably the nucleic acid molecule comprises a sequence having at least about 95% sequence identity to a desired immune related molecule, such as for example Gp49, PIR, PIRA, PIRB, LIR, NKR-P1, NKp46, Digr1, ILT, MIR, KIR, class I MHC.

Percent identity and similarity between two sequences (nucleic acid or polypeptide) can be determined using a mathematical algorithm (see, e.g., *Computational Molecular Biology*, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

To determine the percent identity of two amino acid sequences or of two nucleic acid sequences, the sequences are aligned for optimal comparison purposes (e.g., gaps are introduced in one or both of a first and a second amino acid or nucleic acid sequence for optimal alignment and non-homologous sequences can be disregarded for comparison purposes). The percent identity between the two sequences is a function of the number of identical positions shared by the sequences, taking into account the number of gaps, and the length of each gap which need to be introduced for optimal alignment of the two sequences. The amino acid residues or nucleotides at corresponding amino acid positions or nucleotide positions, respectively, are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

A "comparison window" refers to a segment of any one of the number of contiguous positions selected from the group consisting of from about 25 to about 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art.

For example, the percent identity between two amino acid sequences can be determined using the Needleman and Wunsch algorithm (*J. Mol. Biol.* (48): 444-453, 1970) which is part of the GAP program in the GCG software package (available at http://www.gcg.com), by the local homology algorithm of Smith & Waterman (*Adv. Appl. Math.* 2: 482, 1981), by the search for similarity methods of Pearson & Lipman (*Proc. Natl. Acad. Sci. USA* 85: 2444, 1988) and Altschul, et al. (*Nucleic Acids Res.* 25(17): 3389-3402, 1997), by computerized implementations of these algorithms (GAP, BESTFIT, FASTA, and BLAST in the Wisconsin Genetics Software Package (available from, Genetics Computer Group, 575 Science Dr., Madison, Wis.), or by manual alignment and visual inspection (see, e.g., Ausubel et al., supra). Gap parameters can be modified to suit a user's needs. For example, when employing the GCG software package, a NWSgapdna.CMP matrix and a gap weight of 40, 50, 60, 70, or 80 and a length weight of 1, 2, 3, 4, 5, or 6 can be used. Exemplary gap weights using a Blossom 62 matrix or a PAM250 matrix, are 16, 14, 12, 10, 8, 6, or 4, while exemplary length weights are 1, 2, 3, 4, 5, or 6. The GCG software package can be used to determine percent identity between nucleic acid sequences. The percent identity between two amino acid or nucleotide sequences also can be determined using the algorithm of E. Myers and W. Miller (CABIOS 4: 11-17, 1989) which has been incorporated into the ALIGN program (version 2.0), using a PAM120 weight residue table, a gap length penalty of 12 and a gap penalty of 4.

The nucleic acid and protein sequences of the present invention can further be used as query sequences to perform a search against sequence databases to, for example, identify other family members or related sequences. Such searches can be performed using the NBLAST and XBLAST programs (version 2.0) of Altschul, et al. (*J. Mol. Biol.* 215: 403-10, 1990). BLAST nucleotide searches can be performed with the NBLAST program, with exemplary scores=100, and wordlengths=12 to obtain nucleotide sequences homologous to or with sufficient percent identity to the nucleic acid molecules of the invention. BLAST protein searches can be performed with the XBLAST program, with exemplary scores=50 and wordlengths=3 to obtain amino acid sequences sufficiently homologous to or with sufficient % identity to the proteins of the invention. To obtain gapped alignments for comparison purposes, gapped BLAST can be used as described in Altschul et al. (*Nucleic Acids Res.* 25(17): 3389-3402, 1997). When using BLAST and gapped BLAST programs, the default parameters of the respective programs (e.g., XBLAST and NBLAST) can be used.

The invention also comprises polypeptides, in neural cells, corresponding to a nucleic acid molecule product such as those identified in immune cells, which comprises conservative substitutions that are phenotypically silent. Such substitutions are those that substitute a given amino acid in a polypeptide by another amino acid of like characteristics. Guidance concerning amino acid changes which are likely to be phenotypically silent may be found in Bowie et al., Science 247: 1306-1310,1990, for example. Conservative substitution tables providing functionally similar amino acids are well known in the art (see, e.g., Henikoff and Henikoff, *Proc. Natl. Acad. Sci.* USA 89: 10915-10919,1992) and in the table below.

| Conservative Amino Acid Substitutions | |
| --- | --- |
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual, Second Edition* (1989) Cold Spring Harbor Laboratory Press, Cold Spring Harbor, N.Y. (herein "Sambrook et al., 1989"); *DNA Cloning: A Practical Approach, Volumes I and II* (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

As used herein, the term "fragment or segment", as applied to a nucleic acid sequence, gene or polypeptide, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid or peptide fragments which begin at the amino terminal end of a nucleic acid or protein and end at the carboxy terminal end of the nucleic acid or protein. Each nucleic acid or peptide fragment has at least about one contiguous nucleic acid or amino acid position in common with the next nucleic acid or peptide fragment, more preferably at least about three contiguous nucleic acid bases or amino acid positions in common, most preferably at least about ten contiguous nucleic acid bases amino acid positions in common.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides. Additional preferred embodiments will include lengths in excess of those numbers, e.g., 63, 72, 87, 96, 105, 117, etc. Said fragments may have termini at any pairs of locations, but especially at boundaries between structural domains, e.g., membrane spanning portions.

Homologous nucleic acid sequences, when compared, exhibit significant sequence identity or similarity. The standards for homology in nucleic acids are either measures for homology generally used in the art by sequence comparison or based upon hybridization conditions. The hybridization conditions are described in greater detail below.

As used herein, "substantial homology" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a fragment derived from an immune cell, e.g., T cell receptor, Gp49, PIR, PIRA, PIRB, LIR, NKR-P1, NKp46, Digr1, ILT, MIR, KIR, class I MHC and the like. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203-213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides. The endpoints of the segments may be at many different pair combinations. Chromosomal synteny may be used to further distinguish between homologous genes when there is sufficient evolutionary conservation between the genomes that are being compared, e.g. between mammalian species. A "syntenic homolog" has both sequence identity to the reference gene, and has the corresponding chromosomal location in relation to closely linked genes. Syntenic homologs have a high probability of sharing spatial and temporal localization of gene expression, and of encoding proteins that fill equivalent biological roles.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37 C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349-370.

Cell-Based and Immuno-Assays for Diagnostics and Identifying Immune Related Molecules In another preferred embodiment, the identified genes and gene products can be used to generate antibodies and/or lymphocytes that can function in a cell based or immunoassay to detect a neuronal cell expressing an immune related molecule. Methods for generation of antibodies are well known in the art. Antibodies that specifically bind to an immune related molecule can be obtained commercially or can be prepared using any suitable methods known in the art. See, e.g., Coligan, *Current Protocols in Immunology* (1991); Harlow & Lane, *Antibodies: A Laboratory Manual* (1988); Goding, *Monoclonal Antibodies: Principles and Practice* (2d ed. 1986); and Kohler & Milstein, *Nature* 256:495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

Antibodies can be used in immunoassays to detect, for example, cells expressing the gene products of genes present in immune cells. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

"Immunoassay" is an assay that uses an antibody to specifically bind an antigen (e.g., a marker). The immunoassay is characterized by the use of specific binding properties of a particular antibody to isolate, target, and/or quantify the antigen.

After the antibody is provided, an immune related marker can be detected and/or quantified using any of suitable immunological binding assays known in the art (see, e.g., U.S. Pat. Nos. 4,366,241; 4,376,110; 4,517,288; and 4,837,168). Useful assays include, for example, an enzyme immune assay (EIA) such as enzyme-linked immunosorbent assay (ELISA), a radioimmune assay (RIA), a Western blot assay, or a slot blot assay. These methods are also described in, e.g., *Methods in Cell Biology: Antibodies in Cell Biology*, volume 37 (Asai, ed. 1993); *Basic and Clinical Immunology* (Stites & Terr, eds., 7th ed. 1991); and Harlow & Lane, supra.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or ProteinChip® array described above. The sample is preferably a biological sample taken from a subject.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxidase, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker is incubated simultaneously with the mixture.

Immunoassays can be used to determine presence or absence of a marker in a sample as well as the quantity of a marker in a sample. First, a test amount of a marker in a sample can be detected using the immunoassay methods described above. If a marker is present in the sample, it will form an antibody-marker complex with an antibody that specifically binds the marker under suitable incubation conditions described above. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

The methods for detecting these markers in a sample have many applications. For example, one or more markers can be measured to aid human neural defect diagnosis or prognosis. In another example, the methods for detection of the markers can be used to monitor responses in a subject to treatment, for example of depression. In another example, the methods for detecting markers can be used to assay for and to identify compounds that modulate expression of these markers in vivo or in vitro.

Therapeutics

For therapeutic purposes, immunoreceptor gene products may be generated which include proteins that represent functionally equivalent gene products. For example, an equivalent class I MHC gene product may contain deletions, including internal deletions, additions, including additions yielding fusion proteins, or substitutions of amino acid residues, but that result in a "silent" change, in that the change produces a functionally equivalent class I MHC gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Alternatively, where alteration of function is desired, deletion or non-conservative alterations can be engineered to produce altered, including reduced class I MHC gene products. Such alterations can, for example, alter one or more of the biological functions of the class I MHC gene product. Further, such alterations can be selected so as to generate class I MHC gene products that are better suited for expression, scale up, etc. in the host cells chosen. For example, cysteine residues can be deleted or substituted with another amino acid residue in order to eliminate disulfide bridges. This applies to any immune related molecule and allelic variants thereof, that are identified in neuronal cells.

The class I MHC gene products, peptide fragments thereof and fusion proteins thereof, may be produced by recombinant DNA technology using techniques well known in the art. Thus, methods for preparing the class I MHC gene products, polypeptides, peptides, fusion peptide and fusion polypeptides of the invention by expressing nucleic acid comprising class I MHC gene sequences are described herein. Methods that are well known to those skilled in the art can be used to construct expression vectors comprising class I MHC gene product coding sequences and appropriate transcriptional and translational control signals. These methods include, for example, in vitro recombinant DNA techniques, synthetic techniques, and in vivo genetic recombination. See, for example, the techniques described in Sambrook, et al., 1989, supra, and Ausubel, et al., 1989, supra. Alternatively, RNA capable of encoding class I MHC gene product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the immune related molecules, such as class I MHC gene products. Such host-expression systems represent vehicles by which the coding sequences of interest may be produced and subsequently purified, but also represent cells that may, when transformed or transfected with the appropriate nucleotide coding sequences, exhibit the class I MHC gene product of the invention in situ. The efficiency of expression may be enhanced by the inclusion of appropriate transcription enhancer elements, transcription terminators, etc. (see Bittner, et al., 1987, *Methods in Enzymol.* 153, 516-544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and WI38.

A variety of methods can be employed for the diagnostic and prognostic evaluation of class I MHC mediated neuronal disorders and for the identification of subjects having a predisposition to such disorders.

Such methods may, for example, detect the presence of class I MHC gene mutations, or the detection of either over-, under-, or no expression of class I MHC protein, or mutants, as described in the examples which follow.

Mutations at a number of different genetic loci may lead to phenotypes related to neural disorder, structural and synaptic abnormalities. Ideally, the treatment of patients suffering from such disorders will be designed to target the particular genetic loci comprising the mutation mediating the disorder. Genetic polymorphisms have been linked to differences in drug effectiveness. Thus, identification of alterations in immune related molecules, such as, for example, the class I MHC gene or protein can be utilized to optimize therapeutic drug treatments.

In a preferred embodiment, immune related molecule, such as, for example, Gp49, PIR, PIRA, PIRB, LIR, NKR-P1, NKp46, Digr1, ILT, MIR, KIR, class I MHC, expression levels, mutations, polymorphisms can be detected by using a microassay of for example, class I MHC nucleic acid sequences immobilized to a substrate or "gene chip" for detection of class I MHC molecules (see, e.g. Cronin, et al., 1996, Human Mutation 7:244-255). Preferred methods are detailed in the examples which follow.

The level of class I MHC or any immuno related receptor molecule gene expression, can also be assayed as described in detail in the examples which follow. Additionally, it is possible to perform class I MHC gene expression assays "in situ", i.e., directly upon tissue sections (fixed and/or frozen) of patient tissue obtained from biopsies or resections, such that no nucleic acid purification is necessary. For such in situ procedures (see, for example, Nuovo, G. J., 1992, "PCR In Situ Hybridization: Protocols And Applications", Raven Press, N.Y.). Standard Northern analysis can be performed to determine the level of mRNA expression of the class I MHC gene. Other examples, include but not limited to Gp49, PIR, PIRA, PIRB, LIR, NKR-P1, NKp46, Digr1, ILT, MIR, KIR.

To assess the efficacy of cell-based gene therapy, in vitro immunoassays can be used. Antibodies directed against class I MHC gene products may be used in vitro to determine, for example, the level of class I MHC gene expression achieved in cells genetically engineered to produce class I MHC gene product. In the case of intracellular class I MHC gene products, such an assessment is done, preferably, using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those that are known, or suspected, to express the class I MHC gene. The protein isolation methods employed herein may, for example, be such as those described in Harlow and Lane (1988, "Antibodies: A Laboratory Manual", Cold Spring Harbor Laboratory Press, Cold Spring Harbor, N.Y.). The isolated cells can be derived from cell culture or from a patient. The analysis of cells taken from culture may be a necessary step in the assessment of cells to be used as part of a cell-based gene therapy technique or, alternatively, to test the effect of compounds on the expression of the class I MHC gene or any other immune related molecule.

Preferred diagnostic methods for the detection of immune related molecules, such as, for example, class I MHC gene products, conserved variants or peptide fragments thereof, may involve, for example, immunoassays wherein the class I MHC gene products or conserved variants or peptide fragments are detected by their interaction with an anti-class I MHC gene product-specific antibody. This can be accomplished, for example, by immunofluorescence techniques employing a fluorescently labeled antibody coupled with light microscopic, flow cytometric, or fluorimetric detection. Such techniques are especially preferred for class I MHC gene products that are expressed on the cell surface.

Expression levels and patterns of expression of immunoreceptors are described in the examples which follow. Methods can include for example, antibodies (or fragments thereof) employed histologically, as in immunofluorescence or immunoelectron microscopy, for in situ detection of immune related molecules, such as for example, class I MHC gene products, conserved variants or peptide fragments thereof. In situ detection may be accomplished by removing a histological specimen from a patient, and applying thereto a labeled antibody that binds to a class I MHC polypeptide. The antibody (or fragment) is preferably applied by overlaying the labeled antibody (or fragment) onto a biological sample. Through the use of such a procedure, it is possible to determine not only the presence of the class I MHC gene product, conserved variants or peptide fragments, but also its distribution in the examined tissue. Using the present invention, those of ordinary skill will readily recognize that any of a wide variety of histological methods (such as staining procedures) can be modified in order to achieve in situ detection of a class I MHC gene product.

Immunoassays for immune related molecules, such as for example, class I MHC gene products, conserved variants, or peptide fragments thereof will typically comprise incubating a sample, such as a biological fluid, a tissue extract, freshly harvested cells, or lysates of cells in the presence of a detectably labeled antibody capable of identifying class I MHC gene product, conserved variants or peptide fragments thereof, and detecting the bound antibody by any of a number of techniques well-known in the art.

Identification of Compounds Binding to Immune Related Molecules.

The following assays can be used to identify compounds that bind to an immunoreceptor gene product, compounds that bind to intracellular proteins, or portions of proteins that interact with, for example class I MHC gene product, compounds that interfere with the interaction of a class I MHC gene product with intracellular proteins and compounds that modulate the activity of the class I MHC gene (i.e., modulate the level of class I MHC gene expression and/or modulate the level of class I MHC gene product activity). Such compounds may include, but are not limited to, small organic molecules, such as ones that are able to cross the blood-brain barrier, gain entry into an appropriate cell, for example a neuronal cell, and affect expression of the class I MHC or immunoreceptor genes or some other gene involved in a class I MHC regulatory pathway, or intracellular proteins.

Such compounds may further comprise compounds, in particular drugs or members of classes or families of drugs, known to ameliorate or exacerbate the symptoms of, for example a neuropsychiatric disorder. Compounds include antidepressants such as lithium salts, carbamazepine, valproic acid, lysergic acid diethylamide (LSD), p-chlorophenylalanine, p-propyldopacetamide dithiocarbamate derivatives e.g., FLA 63; anti-anxiety drugs, e.g., diazepam; monoamine oxidase (MAO) inhibitors, e.g., iproniazid, clorgyline, phenelzine and isocarboxazid; biogenic amine uptake blockers, e.g., tricyclic antidepressants such as desipramine, imipramine arid amitryptiline; serotonin reuptake inhibitors e.g., fluoxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), and dibenzodiazepines (e.g., clozapine); benzodiazepines; dopaminergic agonists and antagonists e.g., L-DOPA, cocaine, amphetamine, α.-methyl-tyrosine, reserpine, tetrabenazine, benzotropine, pargyline; noradrenergic agonists and antagonists e.g., clonidine, phenoxybenzamine, phentolamine, tropolone.

Other compounds include those that are useful in down-regulating immune responses, drugs for treatment of autoimmunity, neurological disorders and the like.

In vitro systems may be designed to identify compounds capable of binding, for example, the class I MHC gene products of the invention. Compounds identified may be useful, for example, in modulating the activity of unimpaired and/or mutant class I MHC gene products, may be utilized in screens for identifying compounds that disrupt normal class I MHC gene product interactions, or may in themselves disrupt such interactions.

The principle of the assays used to identify compounds that bind to the immune related molecules, such as for example, class I MHC gene product, involves preparing a reaction mixture of the class I MHC gene product and the test compound under conditions and for a time sufficient to allow the two components to interact and bind, thus forming a complex that can be removed and/or detected in the reaction mixture. These assays can be conducted in a variety of ways. For example, one method to conduct such an assay involves anchoring an class I MHC gene product or a test substance onto a solid support and detecting class I MHC gene product/test compound complexes formed on the solid support at the end of the reaction. In one embodiment of such a method, the class I MHC gene product may be anchored onto a solid support, and the test compound, which is not anchored, may be labeled, either directly or indirectly. These assays can be conducted using microarray technology.

Methods include use of microtiter plates which are conveniently utilized as the solid support. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface comprising the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Any method suitable for detecting protein-protein interactions may be employed for identifying, for example, class I MHC gene product-protein interactions.

Among the traditional methods that may be employed are co-immunoprecipitation, cross-linking and co-purification through gradients or chromatographic columns. Utilizing procedures such as these allows for the identification of proteins, including intracellular proteins, that interact with class I MHC gene products. Once isolated, such a protein can be identified and can be used in conjunction with standard techniques, to identify proteins it interacts with. For example, at least a portion of the amino acid sequence of a protein that interacts with the class I MHC gene product can be ascertained using techniques well known to those of skill in the art, such as via the Edman degradation technique (see, e.g., Creighton, 1983, "Proteins: Structures and Molecular Principles," W.H. Freeman & Co., N.Y., pp. 34-49). The amino acid sequence obtained may be used as a guide for the generation of oligonucleotide mixtures that can be used to screen for gene sequences encoding such proteins. Screening may be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis, et al., eds. Academic Press, Inc., New York).

Additionally, methods may be employed that result in the simultaneous identification of genes that encode a protein which interacts with an class I MHC gene product. These methods include, for example, probing expression libraries with labeled class I MHC gene product, using class I MHC gene product in a manner similar to the well known technique of antibody probing of λ.gt11 libraries.

In another aspect of the invention, assays are provided for compounds that interact with immunoreceptor gene products for use in identifying possible therapeutic drugs. For purposes of this discussion, the macromolecules or drugs are referred to herein as "binding partners". Compounds that also disrupt immune related molecules, such as, for example, class I MHC gene product binding to a binding partner may be useful in regulating the activity of the class I MHC gene product.

For brevity of this discussion, the example used for an immune related molecule will refer to a class I MHC molecule. The basic principle of an assay system used to identify compounds that interfere with the interaction between the class I MHC gene product and a binding partner or partners involves preparing a reaction mixture comprising the class I MHC gene product and the binding partner under conditions and for a time sufficient to allow the two to interact and bind, thus forming a complex. See, for example U.S. Pat. No. 5,734,023, which is incorporated herein, in its entirety. In order to test a compound for inhibitory activity, the reaction mixture is prepared in the presence and absence of the test compound. The test compound may be initially included in the reaction mixture, or may be added at a time subsequent to the addition of class I MHC gene product and its binding partner. Control reaction mixtures are incubated without the test compound or with a compound which is known not to block complex formation. The formation of any complexes between the class I MHC gene product and the binding partner is then detected. The formation of a complex in the control reaction, but not in the reaction mixture comprising the test compound, indicates that the compound interferes with the interaction of the class I MHC gene product and the binding partner. Additionally, complex formation within reaction mixtures comprising the test compound and normal class I MHC gene product may also be compared to complex formation within reaction mixtures comprising the test compound and a mutant class I MHC gene product. This comparison may be important in those cases wherein it is desirable to identify compounds that disrupt interactions of mutant but not normal class I MHC gene product.

The assay for compounds that interfere with the interaction of the class I MHC gene products and binding partners can be conducted in a heterogeneous or homogeneous format. Heterogeneous assays involve anchoring either the class I MHC gene product or the binding partner onto a solid support and detecting complexes formed on the solid support at the end of the reaction. In homogeneous assays, the entire reaction is carried out in a liquid phase. In either approach, the order of addition of reactants can be varied to obtain different information about the compounds being tested. For example, test compounds that interfere with the interaction between the class I MHC gene products and the binding partners, e.g., by competition, can be identified by conducting the reaction in the presence of the test substance; i.e., by adding the test substance to the reaction mixture prior to, or simultaneously with, the class I MHC gene product and interactive intracellular binding partner. Alternatively, test compounds that disrupt preformed complexes, e.g., compounds with higher binding constants that displace one of the components from the complex, can be tested by adding the test compound to the reaction mixture after complexes have been formed.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex formation or that disrupt preformed complexes can be identified. Other methods well known in the art for drug screening can be used.

Assays that identify compounds that alter expression levels or patterns of expression and neural cell plasticity can be cell-based and animal model-based. Identification of such compounds can be used as part of a therapeutic method for the treatment of the disorder.

First, cell-based systems can include, for example, recombinant or non-recombinant cell, such as cell lines, that express genes which include, but are not limited to Gp49, PIR, PIRA, PIRB, LIR, NKR-P1, NKp46, Digr1, ILT, MIR, KIR, class I MHC.

In utilizing such cell systems, cells that express, for example, class I MHC, may be exposed to a compound suspected of exhibiting an ability to alter expression levels of immunoreceptors, such as for example, class I MHC, at a sufficient concentration and for a sufficient time to elicit such a change in expression in the exposed cells. After exposure, the cells can be assayed to measure alterations in the expression of the class I MHC gene, e.g., by assaying cell lysates for class I MHC mRNA transcripts (e.g., by Northern analysis) or for class I MHC gene products expressed by the cell; compounds that modulate expression of the class I MHC gene are good candidates as therapeutics.

In addition, animal-based systems or models for class I MHC, such as those described in the examples can be used. Such animal models may be used as test substrates for the identification of drugs, pharmaceuticals, therapies and interventions. For example, animal models may be exposed to a compound suspected of exhibiting an ability to affect immunoreceptor expression, neural cell plasticity and the like, at a sufficient concentration and for a sufficient time to elicit any changes. The response of the animals to the exposure may be monitored by assays as described in the examples which follow.

In another aspect of the invention it is desirable to correct abnormal immunoreceptor levels of expression or abnormal expression patterns. For example, Gp49, PIR, PIRA, PIRB, LIR, NKR-P1, NKp46, Digr1, ILT, MIR, KIR, class I MHC gene sequences or portions thereof can be used in gene replacement therapy. Specifically, one or more copies of a normal class I MHC gene or a portion of the class I MHC gene that directs the production of a class I MHC gene product exhibiting normal class I MHC gene function, may be inserted into the appropriate cells within a patient, using vectors that include, but are not limited to adenovirus, adeno-associated virus, and retrovirus vectors, in addition to other particles that introduce DNA into cells, such as liposomes. Preferably the vector is herpes simplex virus vector, such as that described in U.S. Pat. Nos. 5,501,979 and 5,661,033, which are herein incorporated by reference in their entirety.

Since it is desirable to express any one or more of an immune related molecule in the brain, such gene replacement therapy techniques should be capable of delivering class I MHC gene sequences to these cell types within patients. Thus, in one embodiment, techniques that are well known to those of skill in the art (see, e.g., PCT Publication No. WO89/10134, published Apr. 25, 1988) can be used to enable, for example, class I MHC gene sequences to cross the blood-brain barrier readily and to deliver the sequences to cells in the brain. With respect to delivery that is capable of crossing the blood-brain barrier, viral vectors such as, for example, those described above, are preferable.

In another embodiment, techniques for delivery involve direct administration of such class I MHC gene sequences to the site of the cells in which the class I MHC gene sequences are to be expressed.

Additional methods that may be utilized to increase the overall level of class I MHC gene expression and/or class I MHC gene product activity include the introduction of appropriate class I MHC-expressing cells, preferably autologous cells, and/or stem cells, and/or neural progenitor cells into a patient at positions and in numbers that are sufficient to rectify the expression of class I MHC. Other immune related molecules include but not limited to, Gp49, PIR, PIRA, PIRB, LIR, NKR-P1, NKp46, Digr1, ILT, MIR, KIR and the like.

Such cell-based gene therapy techniques are well known to those skilled in the art, see, e.g., Anderson, U.S. Pat. No. 5,399,349.

Additionally, compounds, such as those identified via techniques such as those described, above, that are capable of modulating class I MHC gene product activity can be administered using standard techniques that are well known to those of skill in the art. In instances in which the compounds to be administered are to involve an interaction with brain cells, the administration techniques should include well known ones that allow for a crossing of the blood-brain barrier.

Other Methods for Identifying Potential Drug Candidates.

In a preferred embodiment, potential drug candidates could modulate expression of immune related molecules in neuronal cells similar to the regulation in the immune system. For example, molecules such as cytokines.

The invention provides a method for identifying a modulator of an identified immune molecule in a neuronal cell, by for example, administering to a neuronal cell a desired compound and measuring the levels of the immune molecule. Simultaneously, the effects of a compound on the same molecule in an immune cell, are compared to the neuronal cell. The method comprises providing a neuronal cell comprising a nucleic acid encoding an immune related molecule, such as for example class I MHC, exposing the neuronal cell to an agent, and identifying an agent producing a change in one or more of: levels of class I MHC encoding transcripts, levels of cell surface class I MHC protein and the like. The results are compared to an immune cell. Detection of expression levels have been described infra.

In another aspect of the invention, modulators are screened for, preferably in cell based assays, for those which alter proinflammatory cytokine production in immune cells to identify modulators which alter the expression of an immune related molecule in an immune cell known to be affected by such an agent. In this aspect, the assay described above is performed in reverse order; e.g., the effect of cytokine production is screened for first and then agents identified as modulators of cytokine production are selected for further development based on their ability to alter the expression of, for example, class I MHC. Compounds which are known modulators of cytokine production may be assayed directly to determine their effects on, for example, class I MHC expression in neuronal cells.

Robotic systems for performing the assays may be used as are known in the art and described in, for example, U.S. Published Application 20020090320.

Assays may be performed in microtiter plates, in microfabricated devices, or in other containers or on substrates that facilitate handling of large numbers of samples in parallel.

Modulators of immune related molecules include, but are not limited to: small molecules, antibodies, peptides, nucleic acids, protein or nucleic acid aptamers, antisense molecules, ribozymes, triple helix molecules, carbohydrates, and the like. Preferred modulators include those that up-regulate an immune related molecule, such as for example, one involved in neural plasticity or in other cases a down regulator, such as for example a compound that inhibits neuronal cell plasticity.

Libraries of compounds may be screened to identify modulators. There are a number of different libraries used for the identification of small molecule modulators, including: (1) chemical libraries, (2) natural product libraries, and (3) combinatorial libraries comprised of random peptides, oligonucleotides or organic molecules. Chemical libraries consist of random chemical structures, some of which are analogs of known compounds or analogs of compounds that have been identified as "hits" or "leads" in other drug discovery screens, some of which are derived from natural products, and some of which arise from non-directed synthetic organic chemistry. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see *Science* 282: 63-68 (1998). Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8: 701-707 (1997). Identification of modulators through use of the various libraries described herein permits modification of the candidate "hit" (or "lead") to optimize the capacity of the "hit" to modulate activity. Compound libraries may be purchased commercially (e.g., such as LeadQuest™-libraries from Tripos (St. Louis, Mo.)) or may be synthesized using methods well known in the art.

Still other candidate modulators contemplated by the invention can be designed (e.g., by in silico modeling) and include soluble forms of binding partners of immune related molecules, as well as such binding partners which are chimeric, or fusion, proteins. A "binding partner" as used herein broadly comprises non-peptide modulators, as well as such peptide modulators which are natural binding partners of for example, class I MHC.

As an example, Tables 1 through 4 lists a number of genes and/or proteins that may be modulated by different drugs; table 1 (CD markers), table 2 (adhesion molecules) table 3 (chemokines and chemokine receptors), and table 4 (interleukins and their receptors). Also included are the genes encoding the immunoglobulin E (IgE) and the IgE-receptor (FcεRIα) as well as the genes for the other immunoglobulins, $IgG_{(1-4)}$, $IgA_1$, $IgA_2$, IgM, IgE, and IgD encoding free and membrane bound immunoglobulins and the genes encoding their corresponding receptors.

TABLE 1

| CD markers |
|---|
| CD1a-d |
| CD2 |
| CD3 |
| CD4 |
| CD5 |
| CD6 |
| CD7 |
| CD8 |
| CD9 |
| CD10 |
| CD11a |
| CD11b |
| CD11c |
| CDw12 |
| CD13 |
| CD14 |
| CD15 |
| CD16 |
| CDw17 |
| CD18 |
| CD19 |
| CD20 |
| CD21 |
| CD22 |
| CD23 |
| CD24 |
| CD25 |
| CD26 |
| CD27 |
| CD28 |
| CD29 |
| CD30 |
| CD30 |
| CD31 |
| CD32 |
| CD33 |
| CD34 |
| CD35 |
| CD36 |
| CD37 |
| CD38 |
| CD39 |
| CD40 |
| CD41 |
| CD42a-d |
| CD43 |
| CD44 |
| CD45 |
| CD46 |

TABLE 1-continued

| CD markers |
|---|
| CD47 |
| CD48 |
| CD49a-f |
| CD50 |
| CD51 |
| CD52 |
| CD53 |
| CD54 |
| CD55 |
| CD56 |
| CD57 |
| CD58 |
| CD59 |
| CDw60 |
| CD61 |
| CD62 |
| CD62L |
| CD62P |
| CD63 |
| CD64 |
| CD65 |
| CD66a-e |
| CD67 |
| CD68 |
| CD69 |
| CD70 |
| CD71 |
| CD72 |
| CD73 |
| CD74 |
| CDw75 |
| CDw76 |
| CD77 |
| CDw78 |
| CD79a,b |
| CD80 |
| CD81 |
| CD82 |
| CD83 |
| CDw84 |
| CD85 |
| CD86 |
| CD87 |
| CD88 |
| CD89 |
| CD90 |
| CD91 |
| CDw92 |
| CD93 |
| CD94 |
| CD95 |
| CD96 |
| CD97 |
| CD98 |
| CD99 |
| CD100 |
| CD101 |
| CD102 |
| CD103 |
| CD104 |
| CD105 |
| CD106 |
| CD107a,b |
| CDw108 |
| CD109 |
| CD110 |
| CD111 |
| CD112 |
| CD113 |
| CD114 |
| CD115 |
| CD116 |
| CD117 |
| CD118 |
| CD119 |
| CD120a,b |
| CD121 |
| CD122 |

TABLE 1-continued

CD markers

CDw123
CD124
CDw125
CD126
CD127
CDw128
CD129
CD130
CDw131
CD132
CD133
CD134

TABLE 2

Adhesion molecules

| | | | | |
|---|---|---|---|---|
| L-selectin | TCRγ/δ | BB-1 | Integrin α7 | Integrin α6 |
| P-selectin | CD28 | N-cadherin | Integrin α8 | Integrin β5 |
| E-selectin | LFA-3 | E-cadherin P-cadherin | IntegrinαV | Integrin αV |
| HNK-1 | PECAM-1 | | Integrin β2 | Integrin β6 |
| Sialyl- | VCAM-1 | Integrin β1 | Integrin αL | Integrin αV |
| | ICAM-2 | Integrin α1 | IntegrinαM | Integrin β7 |
| Lewis X | ICAM-3 | Integrin α2 | IntegrinαX | IntegrinαIEL |
| | Leukosialin | Integrin α3 | Integrin β3 | Integrin α4 |
| CD15 | HCAM | Integrin α4 | IntegrinαV | Integrin β8 |
| LFA-2 | CD45RO | Integrin α5 | IntegrinαIib | Integrin αV |
| CD22 | CD5 | Integrin α6 | | |
| ICAM-1 | HPCA-2 | | Integrin β4 | |
| N-CAM | | | | |
| Ng-CAM | | | | |
| TCRα/β | | | | |

TABLE 3

Chemokines and Chemokine receptors

| C-X-C chemokines | C-C chemokines | C chemokines | Chemokine Receptors |
|---|---|---|---|
| IL-8 | MCAF/MCP-1 | ABCD-1 | Lympho- CCR1 |
| NAP-2 | MIP-1 α,β | LMC | tactin CCR2 |
| GRO/MGSA | RANTES | AMAC-1 | CCR3 |
| γ IP-10 | I-309 | NCC-4 | CCR4 |
| ENA-78 | CCF18 | LKN-1 | CCR5 |
| SDF-1 | SLC | STCP-1 | CCR6 |
| I-TAC | TARC | TECK | CCR7 |
| LIX | PARC | EST | CCR8 |
| SCYB9 | LARC | MDC | CXCR1 |
| B cell-attracting chemokine 1 | EBI 1 | Eotaxin | CXCR2 |
| | HCC-1 | | CXCR3 |
| | HCC-4 | | CXCR4 |
| | | | CXCR5 |
| | | | CX₃CR |

TABLE 4

Interleukins and their receptors

| | | | | |
|---|---|---|---|---|
| G-CSF | IL-2 Rα | IL-8 | IL-16 | TGF-β1 |
| G-CSF R | IL-2 Rβ | IL-9 | IL-17 | TGF-β1,2 |
| GM-CSF | IL-2 Rγ | IL-9 R | IL-18 | TGF-β2 |
| IFN-γ | IL-3 | IL-10 | PDGF | TGF-β3 |
| IGF-I | IL-3 Rα | IL-10 R | PDGF A Chain | TGF-β5 |
| IGF-I R | IL-4 | IL-11 | PDGF-AA | LAP TGF-β1 |
| IGF-II | IL-4 R | IL-11 R | PDGF-AB | Latent TGF-β1 |
| IL-1α | IL-5 | IL-12 | PDGF B Chain | TGF-β bpl |
| IL-1α | IL-5 Rα | IL-12 p40 | PDGF-BB | TGF-β RII |
| IL-1 RI | IL-6 | IL-12 p70 | PDGF Rα | TGF-β RIII |
| IL-1 RII | IL-6 R | IL-13 | PDGF Rβ | |
| IL-1rα | IL-7 | IL-13 Rα | TGF-α | |
| IL-2 | IL-7 R | IL-15 | TGF-β | |

TABLE 5

Natural Killer Receptors and related receptors detected in neurons:

| | |
|---|---|
| Gp49 family. | Three gene family. Homology with human KIR family. Some KIRs interact directly with MHC class I. In situ hybridization data indicates expression in mouse olfactory bulb and cerebellum. |
| PIR family. | Multiple genes. Similar in structure and some homology to human ILT family. Located on mouse chromosome 7 region that is syntenic to human chromosome 19, where ILT genes reside. Some ILTs interact directly with MHC class I proteins. In situ hybridization data indicates expression in mouse olfactory bulb and cerebellum. |
| NKR-P1. | Three genes in mouse. Activating and Inhibitory Natural Killer receptors. In situ hybridization data indicates expression in mouse olfactory bulb and cerebellum. |
| NKp46. | Interacts with CD3 zeta. Activating Natural Killer Cell receptor. In situ hybridization data indicates expression in mouse olfactory bulb and cerebellum. |
| Digr1. | Preferentially expressed on antigen presenting cells in immune system. Similar in structure to polymeric immunoglobulin receptors and human CMFR-35. Expression in cerebellum, striatum, hippocampus, and olfactory bulb. |

It should be appreciated that in the above tables 1 through 5, an indicated gene means the gene and all currently known variants thereof, including the different mRNA transcripts to which the gene and its variants can give rise, and any further gene variants which may be elucidated. In general, however, such variants will have significant homology (sequence identity) to a sequence of a table above, e.g. a variant will have at least about 70 percent homology (sequence identity) to a sequence of the above tables 1-5, more typically at least about 75, 80, 85, 90, 95, 97, 98 or 99 homology (sequence identity) to a sequence of the above tables 1-5. Homology of a variant can be determined by any of a number of standard techniques such as a BLAST program.

Sequences for the genes listed in Tables 1-5 can be found in GenBank (http://www.ncbi.nlm.nih.gov/). The gene sequences may be genomic, cDNA or mRNA sequences. Preferred sequences are mammalian genes comprising the complete coding region and 5' untranslated sequences. Particularly preferred are human cDNA sequences.

The methods of the invention can be used to screen for antisense molecules that inhibit the functional expression of one or more mRNA molecules that modulate immune related molecule expression. An antisense nucleic acid molecule may be constructed in a number of different ways provided that it is capable of interfering with the expression of a target protein. Typical antisense oligonucleotides to be screened preferably are 30-100 nucleotides in length. The antisense nucleic acid molecule generally will be substantially identical (although in antisense orientation) to the target immune related molecule sequence. The minimal identity will typically be greater than about 80%, greater than about 90%, greater than about 95% or about 100% identical.

Nucleic acid modulators also may include ribozymes. Thus, the methods of the invention can be used to screen for ribozyme molecules that inhibit the functional expression of one or more mRNA molecules that encode one or more proteins that modulate immune related molecules. The design and use of target RNA-specific ribozymes is described in Haseloff et al., Nature 334: 585, 1988; see also U.S. Pat. No. 5,646,023, for example. Tablor, et al., Gene 108: 175, 1991, have greatly simplified the construction of catalytic RNAs by combining the advantages of the anti-sense RNA and the ribozyme technologies in a single construct. Smaller regions of homology are required for ribozyme catalysis, therefore this can promote the repression of different members of a large gene family (e.g., Ig family) if the cleavage sites are conserved.

In another preferred embodiment, siRNAs are used to down-regulate, for example, immune related molecules that have been identified as playing a role in a neural disorder. Several methods are available for the construction of siRNAs, including commercial available sources. siRNAs can be constructed using T7 phage polymerase. T7 polymerase is used to transcribe individual siRNA sense and antisense strands, which are then annealed to produce a siRNA. The T7 polymerase can also be used to transcribe siRNA strands that are linked in cis, forming a hairpin structure. The transcribed RNAs are comprised of 5' triphosphate termini or most preferred for a mammalian cell, 5' monophosphates. Successful siRNA-mediated knockdown of mammalian genes has been recently reported.

Another technique for drug screening provides for high throughput screening of compounds having suitable binding affinity to the protein of interest (see, e.g., Geysen et al., 1984, PCT application WO84/03564). In this method, large numbers of different small test compounds are synthesized on a solid substrate. The test compounds are reacted with immune related molecules, or fragments thereof, and washed. A bound immune related molecule is then detected by methods well known in the art. A purified immune related molecule can also be coated directly onto plates for use in the aforementioned drug screening techniques. Alternatively, non-neutralizing antibodies can be used to capture the peptide and immobilize it on a solid support.

Diagnostic and research reagent kits are also provided which include components to determine identity of the immune related molecule in a patient or other test subject. Thus, the kit may contain a sample of the immune related molecule, gene, an allele or fragment thereof, or expression product of the immune related molecule, gene, an allele or fragment thereof. The kit also may contain instructions (written) for conducting the diagnostic assay. The kit also may contain an assay or test support, typically a solid support, and other materials such as positive control samples, negative control samples, cells, enzymes, detection labels, buffers, etc.

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

EXAMPLES

Materials and Methods

Pan-Specific Class I MHC Probes

The pan-specific class I MHC probe was obtained by reverse transcription-polymerase chain reaction (RTPCR) of adult rat spleen total RNA, using primers targeting the α3 domain of the rat class I MHC molecule rat RT1.Aa [nucleotides (nts) 673 to 859 of GenBank accession M31018; primers were 5'-GATGT SACCC TGAGG TGCTG-3' (SEQ ID NO.: 1) and 5'-GGCAT GTGTA MYTCT GCTCC-3' (SEQ ID NO.: 2)]. The resultant clone RATMHC1 exhibited greater than 95% homology with all mouse class Ia, as well as many class Ib MHC sequences. Subclass-specific class I MHC probes were cloned from mouse CNS by RT-PCR of C57BL/6 mouse hippocampal RNA; primers targeted a segment that varies considerably among class Ia and Ib subfamily members [nts 143 to 463 of GenBank accession U47325 (H-2 Db); primers were 5'-NNGTN GGCTA YGTKG ACRAC-3' (SEQ ID NO.: 3) and 5'-KYRGG TYYTC RTTCA GGG-3' (SEQ ID NO.: 4)]. Clones corresponding to H-2 Db, H-2 Kb(12), Qa-1b, and T22b [J. L. Lalanne et al., Cell 41, 469 (1985); L. Van Kaer et al., Immunol. Rev. 120, 89 (1991)] were identified via BLAST database comparison. Cloning of CD3 (from mouse spleen RNA and in situ hybridization analysis were carried out as described (10).

Cross-hybridization between D, Qa-1, and T22 probes was minimal, as assessed by cross-competition studies: co-hybridization of each labeled riboprobe with a 10,000-fold mass excess of homologous unlabeled transcript abolished all signal, whereas co-hybridization with an excess of the other two unlabeled transcripts resulted in little if any alteration in the hybridization pattern.

Surgical Procedures

All surgeries on postnatal mice were performed according to institutional guidelines and approved protocols. $\beta_2M^{-/-}$ (5× backcrossed to C57BL/6) and $\beta_2M^{-/-}TAP1^{-/-}$ double mutant mice (5× backcrossed to C57BL/6) were obtained from D. Raulet (University of California at Berkeley) (18, 19). $CD3\zeta^{-/-}$ mice (22) (8× backcrossed to C57BL/6) and $RAG1^{-/-}$ mice (38) (10× backcrossed to C57BL/6) were obtained from Jackson Laboratories (Bar Harbor, Me.). As part of the blind study, $\beta_2M^{+/-}$ heterozygotes (from $\beta_2M^{-/-} \times$ C57BL/6 crosses) were intercrossed; $\beta_2M^{+/+}$ and $\beta_2M^{-/-}$ pups were not revealed until after image analysis was complete. P12 mouse pups were anesthetized with isoflurane, and one eye was injected with 1 to 2 μl WGA-HRP (4 to 10% in saline; L7017 from Sigma, St. Louis, Mo., or PL-1026 from Vector Laboratories, Burlingame, Calif.). After 22 to 26 hours, 50-μm brain sections were prepared for histology essentially as described (9); the nitroprusside solution used to stabilize the reaction product was ice-cold and included 10 mM sodium acetate (pH 3.3). For electron microscopy of $\beta_2M^{-/-}TAP1^{-/-}$ mice, P24 animals were perfused first with buffer (0.1 M sodium cacodylate pH 7.35, 5 U/ml heparin) and then 1% paraformaldehyde, 2% glutaraldehyde, 0.2% acrolein, and 4 mM $CaCl_2$ in buffer. The thalamus was fixed overnight at 4° C.; dLGN was isolated from 150-gm Vibratome sections and processed for electron microscopy.

Image Analyses

The following series of steps was carried out on all slide sets by an observer blind to genotype. Only sets exhibiting equivalent degrees of anterograde labeling were selected for analysis. Eight-bit TIFF images comprising the dLGN were acquired on a Macintosh-linked charge-coupled device camera (MTI VE1000) attached to a Nikon Microphot FXA. Using NIH Image (v1.62b7), images of the dLGN ipsilateral and contralateral to the injected eye were cropped to exclude ventral LGN, intrageniculate leaf and extrageniculate optic tract; images of ipsilateral dLGN were also modified to eliminate the optic tract running above the dLGN. NIH Image macros were used to eliminate background blood vessel-derived staining (very heavily stained blood vessels were removed by hand) and to calculate areas occupied by retinal projections. For each brain, an internally controlled measure of the area occupied by the ipsilateral projection was obtained by dividing the average of the four largest ipsilateral areas (corresponding to the middle third of the dLGN) by the average of the four largest total dLGN areas (assessed by the outer boundaries of the contralateral projection zones). Sections in FIG. 3, A to E, were photographed in both bright-field and dark-field optics. Although dark-field optics are more sensitive and reveal lightly labeled regions as white, very heavily labeled regions become saturated and appear black. Therefore, for accuracy, composites of bright-field and dark-field images of the same section were constructed to ensure that heavily labeled regions appeared white, while detailed information about lightly-labeled regions revealed in dark-field was preserved.

Method for Determining Hippocampal Synaptic Plasticity

Slices of mouse brain 400 µm thick (from 8- to 17-week-old animals, killed with halothane) were maintained at 25° C. in a submerged recording chamber (perfused at 2 to 3 ml/min) with artificial cerebrospinal fluid (ACSF: 126 mM NaCl, 2.5 mM KCl, 1.25 mM $NaH_2PO_4$, 1.3 mM $MgSO_4$, 2.5 mM $CaCl_2$, 26 mM $NaHCO_3$, and 10 mM glucose). Connections to the CA3 region of the hippocampus were cut, and 100 µM picrotoxin (Sigma) was added to the bath ACSF. Stainless-steel bipolar electrodes were used to stimulate Schaffer collateral/commissural fibers; glass microelectrodes filled with ACSF (2 to 6 MΩ) were inserted into the stratum radiatum to record currents from populations of CA1 pyramidal cells. Test pulses (0.033 Hz) were applied at a stimulation intensity required to produce an fEPSP that was 30% (for 100 Hz stimulation) or 50% (for 0.5 and 1 Hz stimulation) of the maximal response for each recording. High-frequency stimulation (tetanus) consisted of four trains of 100 pulses at 100 Hz (inter-train interval 15 s), applied at time 0. All values are reported as means±SEM, n is the number of slices (one slice per mouse). Data collection was performed by an observer blind to genotype. Before the blind was dropped, recordings were omitted from analysis if the extracellular resistance changed significantly (3/94) or if the stimulating electrode had visibly drifted over the course of the recording (4/94). LTP was calculated as the average of responses between 0 and 60 min after tetanus, normalized to a 15-min pretetanus control period. Stimulus intensity was relatively high because of the use of electrodes with uninsulated tips to maximize the number of fibers stimulated. Stimulus artifacts were clearly complete well before fEPSP onset and so were easily excluded from analysis. In experiments using D-APV, drug was added at least 30 min before tetanic stimulation and was present throughout the entire recording. Statistical significance was assessed by two-tailed one-way ANOVA or Student's t-test.

Example 1

Detection of Class I MHC

Although class I MHC is primarily known for its function in cell-mediated immune recognition, class I MHC molecules can play roles in structural and synaptic remodeling in the developing and mature CNS. Since numerous class I MHC genes exist in the mouse genome, to determine whether class I MHC and CD3ζ were expressed in the developing mouse CNS, in situ hybridization was performed using the pan specific cDNA probe which was expected to detect many class I MHC molecules, as described in the materials and methods. This probe detected elevated amounts of mRNAs in the dorsal LGN (dLGN) during the first two postnatal weeks, exactly when ganglion cell axons sort into eye-specific layers in the mouse; mRNA levels declined at later ages. This was shown in FIG. 1A, when postnatal days P6 and P40, were compare. Expression was also evident in the ganglion cell layer of the retina as shown in FIG. 1A, P6 eye; in the neocortex in layer 4 at early ages and in deeper layers later, FIG. 1A; and in granule and pyramidal cell layers of the hippocampus, as shown in FIG. 1A, P40, and FIG. 2. CD3ζ mRNA, like that of class I MHC, was expressed in the mouse dLGN during the first two postnatal weeks (FIG. 1B); expression appeared higher medially. CD3ζ mRNA was also detected in small amounts in P40 hippocampus. Therefore, class I MHC and CD3ζ transcripts are present in the developing murine CNS at locations and times consistent with a role for these molecules in activity-dependent structural remodeling and synaptic plasticity.

Figure 2:
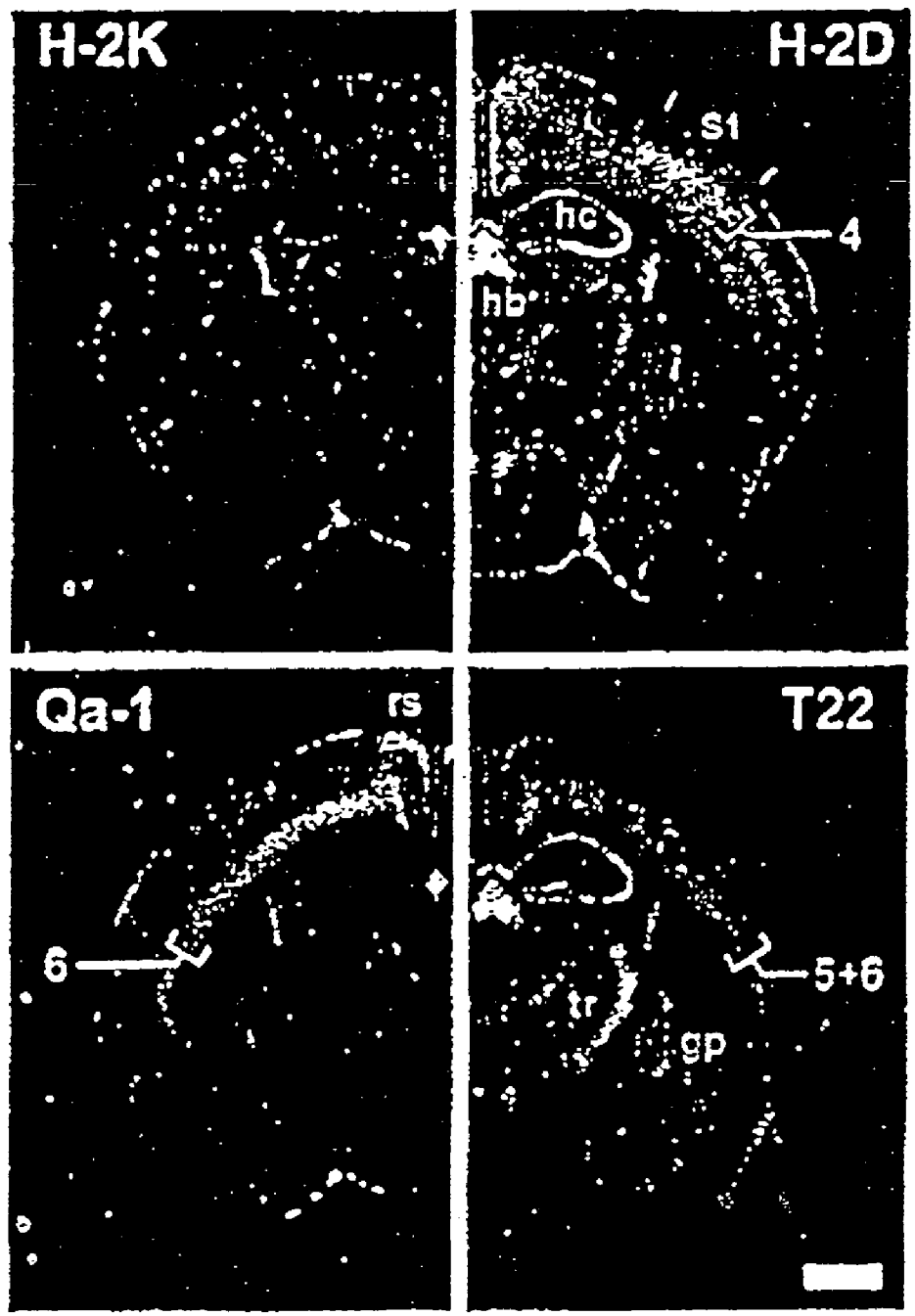
FIG. 2 is a photograph of a tissue section showing the expression of multiple class I MHC subclasses in distinct regions of the mature CNS. Coronal sections of P40 mouse brain analyzed by in situ hybridization, using subclass-specific probes are indicated at the top of each panel. S1 stands for somatosensory cortex; hb stands for habenula; hc stands for hippocampus; rs stands for retrosplenial cortex; tr stands for thalamic reticular nucleus; gp stands for globus pallidus. Numerals (4, 6, 5+6) indicate neocortical layers. Scale bar, 1 mm.

Strikingly, different class I MHC genes are expressed in unique subsets of neurons throughout the mature CNS, as revealed by using pan specific cDNA probes that react more specifically with each of two class Ia (H-2D, H-2K) or two class Ib MHC genes (Qa-1, T22). For example, within the somatosensory cortex, H-2D probe signal was distributed through many layers but was strongest in layer 4; Qa-1 signal was specific to layer 6, and T22 signal was evident in both layers 5 and 6, as shown in FIG. 2. H-2D and T22 signals were both strong in the pyramidal layers of the hippocampus and in the habenula; in contrast, that of Qa-1 was weak in those locations, as shown in FIG. 2. Transcripts detected by the T22 probe were particularly abundant in the thalamic reticular nucleus, globus pallidus, and substantia nigra (shown in FIG. 2). H-2K signal paralleled that of H-2D but was much lower throughout the brain. The distinct expression patterns detected by these probes demonstrated conclusively that several class I MHC mRNA subtypes are differentially expressed by distinct subsets of neurons in the CNS. These findings indicate that there is functional diversity among class Ia and Ib genes within the CNS. Such heterogeneity of function occurs among these genes within the immune system.

Example 2

Class I MHC is Required for Activity-Driven Structural Remodeling and Synaptic Plasticity To determine that class I MHC is required for activity-driven structural remodeling and synaptic plasticity, mice deficient either for cell surface class I MHC expression or for CD3ζ were analyzed. As numerous class I MHC genes may be expressed by specific subsets of neurons (FIG. 2), mice strains, that lack two molecules required for the stable cell-surface expression of nearly all fully assembled class I MHC molecules, were examined. The mouse strains lack β2-microglobulin [β2M, a class I MHC co-subunit, and TAP1 [a component of the transporter that supplies peptides to class I MHC enroute to the cell surface]. β2-M is expressed by neurons in LGN, cortex, and hippocampus and, as in nonneuronal cells, induction of class I MHC on the cell surface of neurons requires expression of β2M and TAP1 mRNAs. In addition, to examine whether CD3ζ-comprising receptors were involved in class I MHC-mediated signaling in the CNS, mice lacking CD3ζ were also analyzed. When raised in a germ-free facility, all mutant mice are outwardly normal and are not obviously different from wild-type mice in weight, body length, appearance, or behavior.

Mice deficient in class I MHC-mediated signaling might have abnormal patterns of retinogeniculate projections because blockade of neural activity simultaneously prevents the segregation of retinal ganglion cell axons into eye-specific layers and reduces class I MHC expression in the LGN. The normal adult mouse dLGN has a small layer that receives inputs from ganglion cells in the ipsilateral eye; inputs from the contralateral eye occupy the remainder of the dLGN (FIG. 3A). The refinement of these eye-specific connections in the mouse occurs between postnatal day 4 (P4) and P8. Examination of the distribution of retinal inputs at P13, was conducted 5 days after segregation was complete, using the anterograde transport of horseradish peroxidase-conjugated wheat germ agglutinin (WGA-HRP) injected into one eye.

Figure 3:
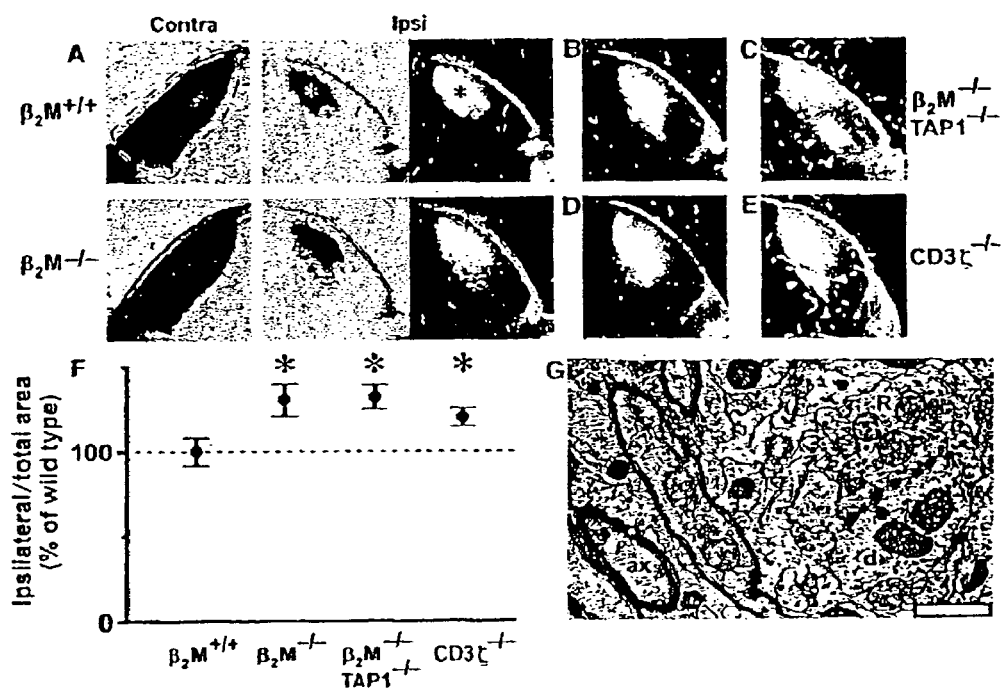
FIGS. 3 D and 3 E are representative (3D) and extreme (3E) examples of the projection in CD3ζ$^{-/-}$ mice. Arrowheads indicate ectopic projections, which appear extensive under the more sensitive dark-field optics. Scale bar, 200 mm.

The data showed that compared with wild-type animals (FIGS. 3, A and F, β2M1/1), the pattern of the retinogeniculate projection was significantly altered in all three mutant genotypes tested. This point is best appreciated by inspecting the size and shape of the ipsilateral retinal projection to the dLGN (FIGS. 3, A to E). Although all mutants still form an ipsilateral patch located approximately normally in the mediodorsal dLGN, the area of this patch was significantly larger in mutant mice and, in extreme cases, was accompanied by multiple ectopic clusters of inputs that were never observed in wildtype mice (FIG. 3, C and E, arrowheads). These ectopic clusters appeared in medial areas of the dLGN, where the highest levels of CD3 mRNA are normally present (compare FIGS. 3, C and E, with FIG. 1A). In these extreme cases, ectopic clusters were also observed in the ipsilateral superior colliculus, another retinorecipient target that expresses low-to-moderate levels of class I MHC mRNA in mouse.

FIG. 3 shows the abnormal retinogeniculate projections but normal dLGN ultrastructure in mice deficient in class I MHC signaling. At P12, one eye was injected with WGA-HRP; after 1 day, anterograde axonal transport results in labeling of the entire retinal projection to the LGN. Labeling pattern in the dLGN is shown in bright-field optics (label is black) or as dark-field composites [label is white]. (A) Representative projection from retina to dLGN contralateral (dashed lines; coronal section; dorsal is up; lateral is left) or ipsilateral to eye injected with WGA-HRP (asterisks indicate labeled area from ipsilateral eye: lateral is to right) in a P13 $β_2M^{+/+}$ wild-type mouse and a $β_2M^{-/-}$ mutant mouse. (B and C) Representative (B) and extreme (C) examples of the projection from the ipsilateral eye observed in $β_2M^{-/-}TAP1^{-/-}$ mice. (D and E) Representative (D) and extreme (E) examples of the projection in $CD3ζ^{-/-}$ mice. Arrowheads indicate ectopic projections, which appear extensive under the more sensitive dark-field optics. Scale bar, 200 mm. (F) Graph of areas (±SEM) occupied by the ipsilateral retinal projection to the LGN for $β_2M^{+/+}$ (wild-type), $β_2M^{-/-}$, $β_2M^{-/-}TAP1^{-/-}$, and CD3ζ-/- mice, normalized to total dLGN area. The ipsilateral projection area in $β_2M^{+/+}$ animals is set as 100% (horizontal dashed line). Asterisks indicate significant differences from $β_2M^{+/+}$ mice (P<0.05, Student's two-tailed t test). (G), Electron micrograph of the dLGN from a $β_2M^{-/-}TAP1^{-/-}$ mouse (at P24), showing a typical R-type synaptic bouton (R) making contacts with a dendrite (d). A well-myelinated axon (ax) is also present in this field. Scale bar, 1 μm.

Example 3

Quantitation of Altered Retinogeniculate Projection

To assess quantitatively the altered retinogeniculate projection in mutant mice, computerized image analysis was used to measure the fraction of dLGN area occupied by the ipsilateral projection. All image analyses were carried out by an observer blind to genotype, as described in the materials and methods. In all mutant genotypes, there was a significant increase in area occupied by the ipsilateral projection over that of wildtype controls [FIG. 3F: $β_2M^{-/-}$, 130.3±7.3% (n=10); $β_2M^{-/-}TAP1^{-/-}$, 133.3±5.7% (n=13); $CD3ζ^{-/-}$, 122.7±4.2% (n=13); wild-type $β_2M^{+/+}$, 100.0±9.1% (n=12); P<0.05, Student's two-tailed t-test]. The data show that class I MHC function is required for the developmental refinement of the retinal projections and the formation of precise eye-specific regions in the LGN.

Although the refinement of retinogeniculate axons was abnormal in mutant mice, many other aspects of LGN development appear to proceed normally. The histological appearance, size, shape, and location of the dLGN and thalamus, as viewed in Nissl-stained sections, were indistinguishable among all experimental groups. The bulk of the ipsilateral projection was positioned, as expected, in the binocular region of the dLGN. At the ultrastructural level, the synaptic organization of the LGN in $β_2M^{-/-}TAP1^{-/-}$ mice appeared qualitatively indistinguishable from that of wild type. Retinogeniculate axons were well-myelinated, and glomeruli and R-type synaptic boutons [hallmarks of retinogeniculate synapses] were present, indicating that normal retinal synapses do form in the LGN (FIG. 3G). These observations show that many activity-independent processes are not perturbed in mice with abnormal class I MHC function.

To determine whether the mutant retinogeniculate phenotypes were secondary to abnormal retinal activity, calcium imaging of mutant retinas revealed spontaneous retinal waves with spatiotemporal properties indistinguishable from those of normal mice. Thus, abnormalities in the mutant retinogeniculate projection are ascribed directly to a loss of class I MHC signaling downstream of neural activity.

Example 4

Altered Synaptic Activity in Mutant Mice

Activity-dependent structural reorganizations during development may arise from cellular mechanisms of synaptic plasticity. Experiments were conducted to determine whether synaptic plasticity is altered in mutant mice. Little is known about such mechanisms in the developing LGN, a well-characterized model system, was used, for studying long-lasting changes in the strength of synaptic transmission: the Schaffer collateral-CA1 synapse of the hippocampus. Class I MHC and CD3ζ were both expressed in the adult hippocampuses shown in FIG. 1. Furthermore, class I MHC immunoreactivity can be detected in synaptosome preparations, suggesting that some class I molecules are synaptically associated. Therefore, hippocampal synaptic plasticity in wild-type and mutant mice was assessed. Data collection was performed by an observer blind to genotype.

Figure 4:
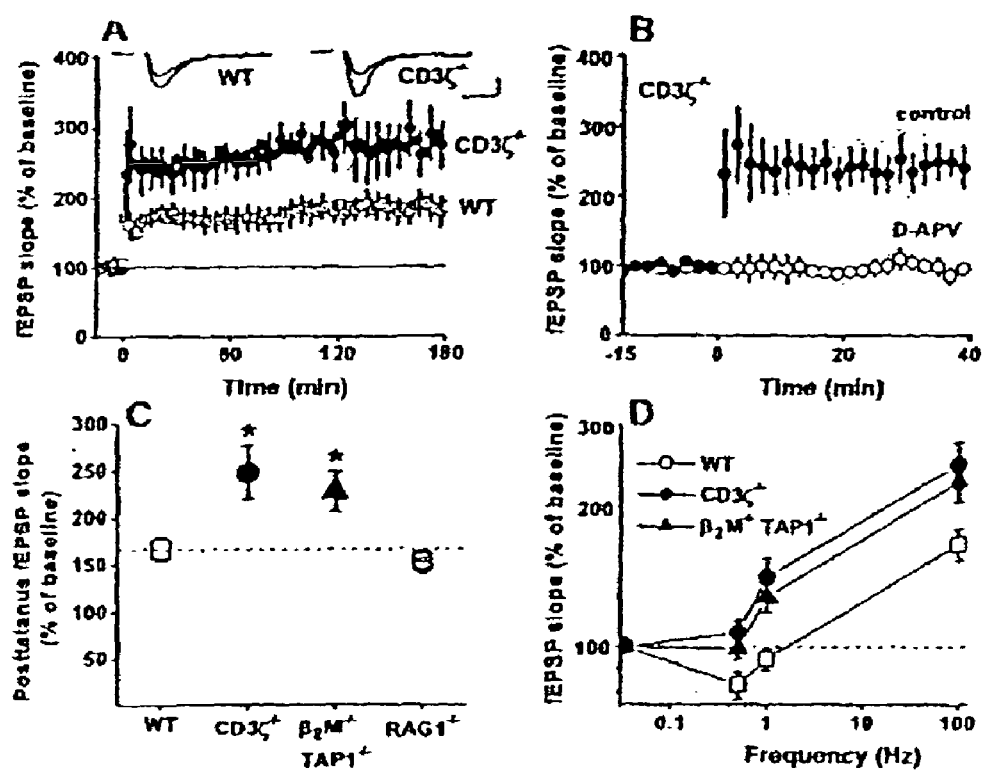
FIG. 4 C shows the graphs summarizing degree of potentiation in wild-type, $\beta_2M^{-/-}$TAP1$^{-/-}$, CD3ζ$^{-/-}$, or RAG1$^{-/-}$ mice after 100-Hz tetanus.
Figure 5:
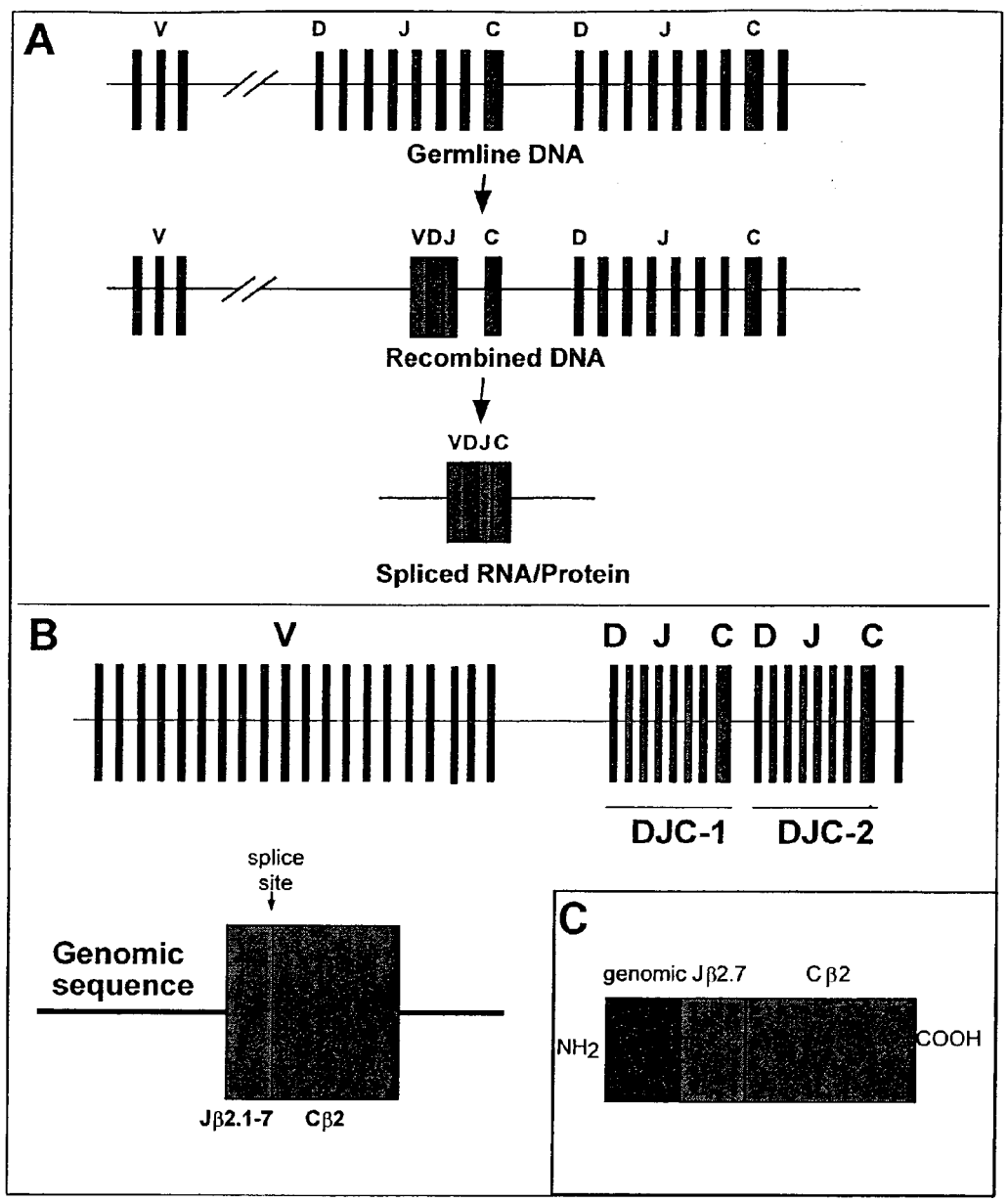
FIGS. 5A-5C is a diagram illustrating TCR beta genomic recombination and splicing to generate a mature T cell receptor.

The results show that in wild-type mice (C57BL/6), tetanic stimulation (4×100 Hz) resulted in a sustained increase in the slope of the field excitatory postsynaptic potential (fEPSP) (167±13% of pretetanus baseline; n=15; FIGS. 4, A and C). In contrast, in $CD3ζ^{-/-}$ mutant animals, LTP in response to the same tetanus was significantly enhanced relative to that in wild-type mice (248±29% of baseline; n=8; P<0.05; FIG. 4, A and C). A similar enhancement of LTP was observed in $β_2M^{-/-}TAP1^{-/-}$ mutant mice (227±22% of baseline; n=10; P<0.05; FIG. 4C). Basal synaptic transmission is not significantly different among all experimental groups. Pretetanus test pulse fEPSP slopes for mice with normal ventricles (millivolts per millisecond) were as follows: wild type, 0.091±0.007 (n=14); $CD3ζ^{-/-}$, 0.091±0.009 (n=8, P=0.95 compared with wild type); $β_2M^{-/-}TAP1^{-/-}$, 0.089±0.010 (n=9, P=0.85). Stimulation intensities required to evoke an fEPSP at 30% of the maximal response (in microamperes) were as follows: wild type, 136±27; $CD3ζ^{-/-}$, 134±24 (P=0.75 compared with wild type); $β_2M^{-/-}TAP1^{-/-}$, 128±17 (P=0.59).

Enhanced LTP in gene knockout animals was not due to changes in inhibition, because $GABA_A$-mediated transmission was blocked with 100 μM picrotoxin in all experiments. Nor was the enhanced LTP due to induction of an N-methyl- D-aspartate (NMDA) receptor-independent form of LTP, because LTP was completely abolished in all genotypes in the presence of the NMDA antagonist 2-amino-5-phosphonovalerate [50 µM D-APV; FIG. 4B]. Posttetanus fEPSP slopes, averaged over 180 min, did not differ significantly from baseline in the presence of 50 µM D-APV: wild type, 107±14% (n=3; P=0.64); CD3$\zeta^{-/-}$, 97±9% (n=3; P=0.93); and $\beta_2$M$^{-/-}$TAP1$^{-/-}$, 106±10% (n=5; P=0.56, Student's t-test).

FIG. 4 shows the enhanced hippocampal LTP in mice deficient either for cell surface class I MHC expression or for CD3z. (A) Field EPSP (fEPSP) slopes in wild-type versus CD3$\zeta^{-/-}$-deficient mice. Tetanus was applied at time 0. (Insets) Superimposed sample fEPSPs recorded 10 min before or 180 min after tetanic stimulation from individual wild-type (left) and CD3$\zeta^{-/-}$, (right) slices. Scale bar, 10 msec/0.25 mV. (B) NMDA receptor dependence of LTP in CD3$\zeta$ deficient mice. Tetanus was applied at time 0 either in the absence [filled circles; from (A)] or presence (hollow circles) of 50 µM D-APV. All points in (A) and (B) are averages of four consecutive fEPSPs (means±SEM, normalized to 15-min baseline) recorded from CA1. (C) Graphs summarizing degree of potentiation in wild-type, $\beta_2$M$^{-/-}$TAP1$^{-/-}$, CD3$\zeta^{-/-}$, or RAG1$^{-/-}$ mice after 100-Hz tetanus.

Data are shown for mice with histologically normal brains. When brains of otherwise normal-appearing animals at age P13 were examined, 52% (16/31) of $\beta_2$M$^{-/-}$TAP1$^{-/-}$ mice and 22% of CD3$\zeta^{-/-}$ mice (10/45) had enlarged lateral ventricles. This phenotype is unlikely to be due to immunocompromise because severely immunodeficient RAG1$^{-/-}$ mice, when co-housed in our facility, do not exhibit this phenotype (0/18). This phenotype also occurs in 57% (12/21) of $\beta_2$M$^{-/-}$TAP1$^{-/-}$ and 20% (2/10) of CD3$\zeta^{-/-}$ adult mice. Although ventricular enlargement does not affect the appearance of the dLGN and thalamus (assessed by Nissl stains), the size, placement, and appearance of extrathalamic structures such as the hippocampus can be altered. In the LTP analysis, animals with enlarged ventricles were treated separately because in these animals, LTP measurements could be confounded by abnormal hippocampal architecture and the known reduction of LTP by hydrocephalus [T. Tsubokawa, Y. Katayama, T. Kawamata, *Brain Inj.* 2, 19 (1988)]. Consistent with the latter idea, LTP at 100 Hz in $\beta_2$M$^{-/-}$TAP1–/– mice with dilated ventricles, while still present, is significantly lower than that of $\beta_2$M$^{-/-TAP}$1$^{-/-}$ mice with normal-appearing brains (168±15% relative to 227±22%; P<0.05). CD3$\zeta^{-/-}$ mice with dilated ventricles also displayed diminished LTP. Asterisks indicate significant differences from wild type (one-way ANOVA, P<0.05).

FIG. 4 D shows the relation (logarithmic plot) between synaptic enhancement and stimulation frequency. Points at 0.033 Hz (test pulse frequency) indicate baseline values (horizontal dashed line). Points at 100 Hz are taken from (C). Values in (C) and (D) are mean fEPSP slopes for each genotype over the 1-hour period following tetanus.

Example 5

LTP Enhancement in RAG-1 Deficient Mice

Since enhancement of LTP seen in the above mouse genotypes is due to some nonspecific effect of immune compromise on the CNS, LTP was examined LTP in a more severely immunodeficient strain of mice that lacks recombination activating gene-1 (RAG1). RAG1 is required for production of B and T cells and is also transcribed by neurons in the CNS. The results showed that LTP in RAG1–/– mice was indistinguishable from that of wild type [153±13% of baseline (n=10), compared with 167±13% in wild type; P=0.48; FIG. 4C], indicating that the LTP abnormalities seen in $\beta_2$M –/–TAP1–/– or CD3$\zeta$–/– mice are specific to their genotypes rather than to immune status.

Example 6

Effect of Stimulation Frequencies on Synaptic Plasticity in Animals Deficient for Class I MHC Signaling Synaptic plasticity in the hippocampus is dependent on stimulation frequency, with high frequencies producing LTP and low frequencies producing LTD. The effects different stimulation frequencies on synaptic plasticity in animals deficient for class I MHC signaling, were determined. The results show that in adult wild-type slices, the delivery of 900 pulses at 0.5 Hz induced significant LTD (82±6% of baseline; n=8; P<0.05; FIG. 4D). In adult slices from both mutant genotypes, however, there was no significant change in fEPSP slope upon 0.5 Hz stimulation [CD3$\zeta$–/–, 107±7% of baseline (n=5, P=0.29); $\beta_2$M –/–TAP1–/–, 99±5% of baseline (n=8, P=0.78); FIG. 4D]. Furthermore, after 900 pulses at 1 Hz, transmission was significantly enhanced over baseline in both CD3$\zeta$–/– (141±14% of baseline, n=5, P<0.05) and $\beta_2$M –/–TAP1–/– slices (128±9%, n=6, P<0.05) but was unchanged in wild-type slices (94±5%, n=14, P=0.41; FIG. 4D). Thus, in mutant mice, LTD could not be detected, and the frequency-response curve of hippocampal synaptic plasticity was consistently shifted across a broad range of stimulation frequencies.

These results show that class I MHC/CD3$\zeta$ signaling is important for mediating activity-dependent synaptic depression, because, in mutants, there is a shift in the bi-directional regulation of synaptic strength [i.e., the frequency response function] that favors potentiation. In the absence of class I MHC or CD3, patterns of neural activity that normally have no effect on synaptic strength or that lead to synaptic depression result, instead, in abnormal synaptic strengthening. Likewise, in the dLGN, enhanced LTP and lack of LTD at the developing retinogeniculate synapse could account for the structural phenotype observed: a persistence of inappropriate connections that would be normally be removed via an activity-dependent process of synaptic weakening during eye-specific segregation.

Example 7

Identification of TCR in Brain Cells

We have found that a least part of the TCR beta locus is expressed by neurons of the mammalian CNS in vivo. The alpha-beta T-cell receptor (TCR) is comprised of alpha and beta receptor subunits, as well as CD3 signaling components. In T-cells, the gene encoding the beta subunit must undergo genomic recombination in order to produce a functional transcript. This process fuses variable (V), diversity (D), and joining (J) regions of the genomic locus. The recombined gene is transcribed, and the transcript is spliced to form a mature mRNA encoding V, D, J and a constant region (C), in frame (FIG. 4A).

Samples from TCR beta knockout mice, in which both constant regions have been removed from the genome, exhibit no in situ hybridization signal, indicating that our probe is specific for TCR beta. RACE techniques, which use PCR to amplify 5' ends of mRNA where only the 3' sequence is known, indicate that brain derived TCR beta is expressed from the DJC-2 region of unrecombined TCR beta loci. All of the transcripts isolated have at their 5' end genomic sequences matching those 5' to one of the six J-beta-2 regions, followed by the J-beta 2-region, which is then spliced to the C-beta-2 constant region (FIG. 4B). In situ hybridization experiments, where probes specific for genomic DJC-1 and DJC-2 regions were used to probe adult mouse brain, confirm that only transcripts from DJC-2 are expressed. Of the six J-beta-2 transcripts, only one, J-beta 2.7, has an in-frame start codon that is both upstream of the J-region and downstream of all in-frame stop codons. J-beta 2.7 encodes a hypothetical protein with 19 amino acid residues at its amino terminus, followed by J-beta 2.7 and C-beta-2 (FIG. 4C). The 19 amino acids of the amino terminus contain a six amino acid hydrophobic stretch, which forms a consensus signal sequence for insertion into the endoplasmic reticulum. Thus, neurons express mRNA for an unrecombined TCR beta receptor.

Example 8

Identification of PirB in the Brain Using a Pan-Specific Pir Probe

Paired immunoglobulin like receptor (PIR) genes are comprised of about 11 genes. They are syntenic with human region which encode Ig-like transcript (ILT) and leukocyte Ig-like receptors (LIR), of class I MHC. PirB phosphorylation is reduced 50% in β2m mice, but not in Tap1 mice.

Figure 6:
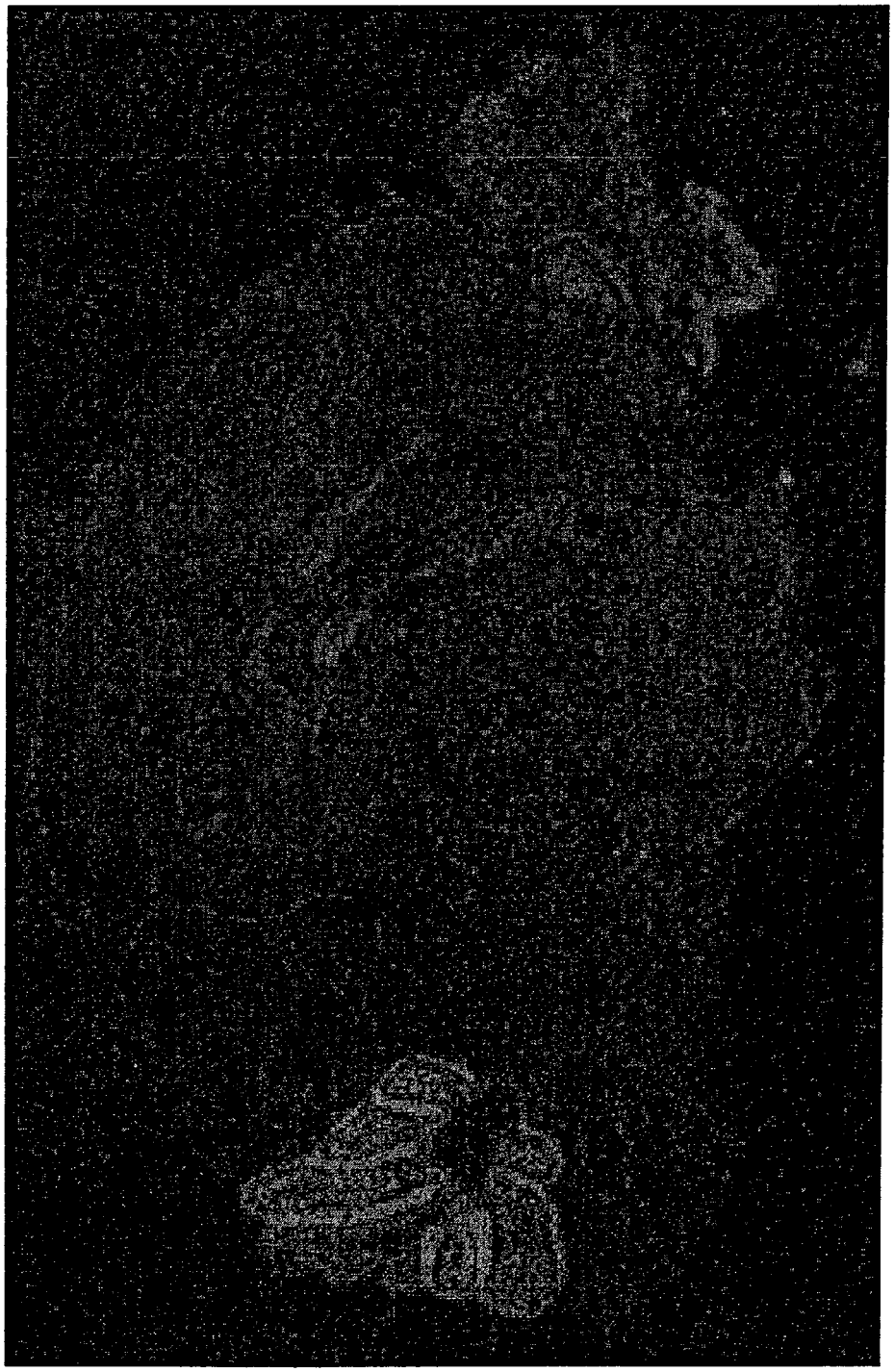
FIG. 6 is a autoradiograph showing the results of in situ hybridization of a postnatal day 7 mouse brain using a pan PIR specific probe which recognizes all Pir mRNA.

Pir was detected in the brains of mice. FIG. 6 are the results of in situ hybridization of a postnatal day 7 mouse brain using a pan PIR specific probe which recognizes all Pir mRNA.

Figure 7:
FIG. 7 is an autoradiograph showing the results of in situ hybridization of an adult mouse brain using a probe which recognizes all Pir mRNA.

FIG. 7 shows the results of in situ hybridization of an adult mouse brain using a probe which recognizes all Pir mRNA.

Figure 8:
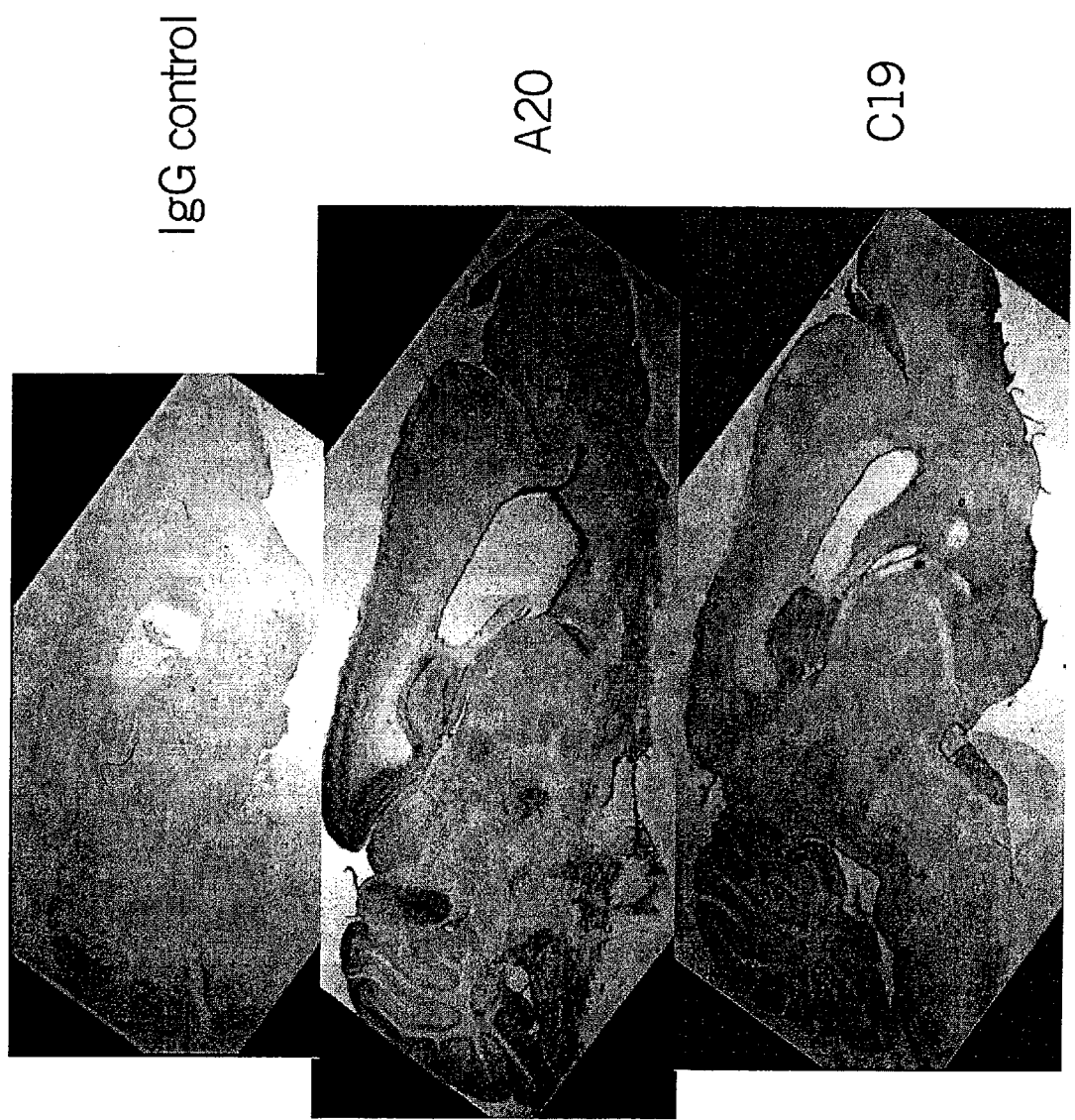
FIG. 8 is a photograph shows the results of immunohistochemistry of an adult mouse brain using Anti-Pir polyclonal antibodies A20 or C19. The control is serum IgG from goat.

FIG. 8 shows the results of immunohistochemistry of an adult mouse brain using Anti-Pir polyclonal antibodies A20 or C19. The control is serum IgG from goat.

Figure 9:
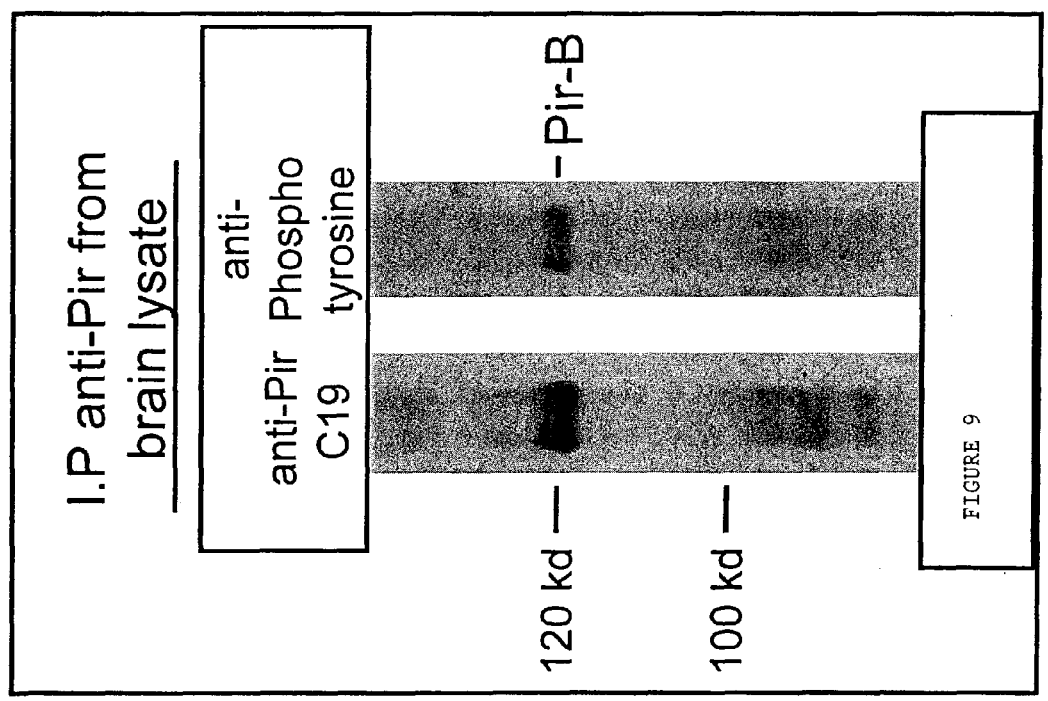
FIG. 9 is a gel showing immunoprecipitation of Pir-B with polyclonal antibody C19 from whole mouse brain. A Western blot was conducted using either C19 anti-Pir (left) or anti-phosphotyrosine.
Figure 10:
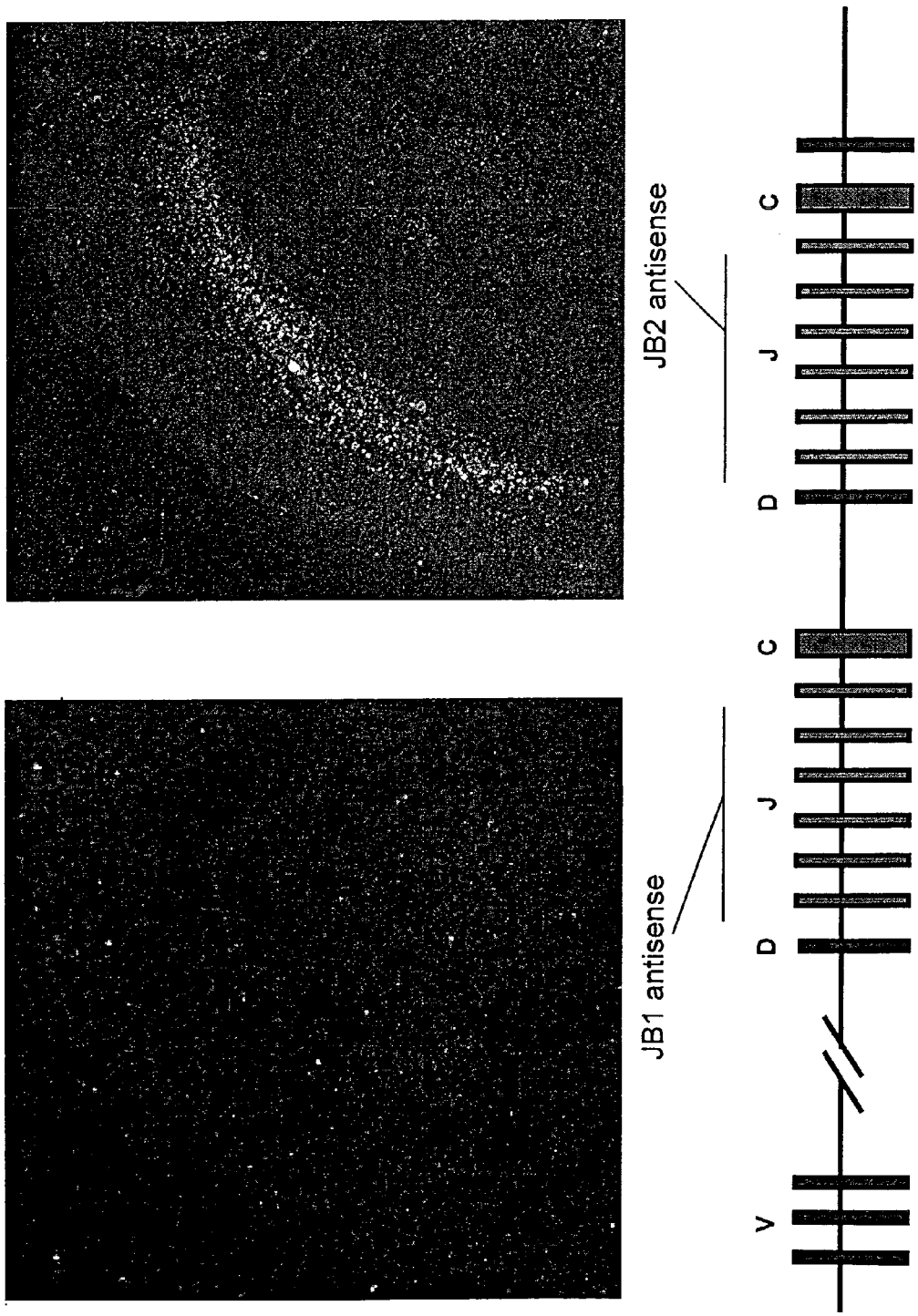
FIG. 10 is an autoradiograph of in situ hybridization with a T cell receptor probe, JB1 (left panel), and a JB2 probe (right panel).
Figure 11:
FIG. 11 shows the results from an in situ hybridization of a mouse brain using probes which hybridize to Pir A and B.
Figure 12:
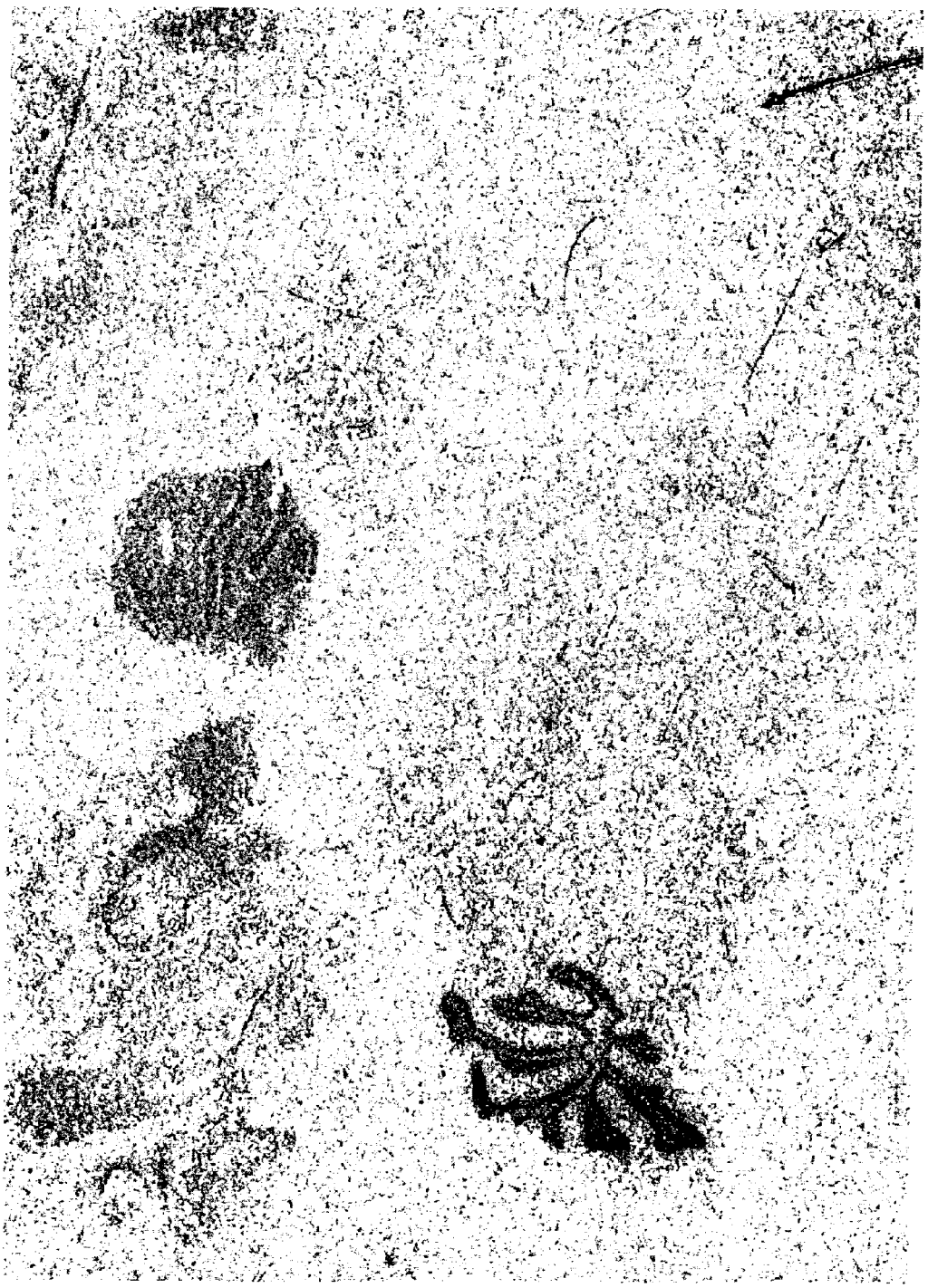
FIG. 12 shows the results from an in situ hybridization of a mouse brain using a probe to detect the presence of GP49 in the brain.
Figure 13:
FIG. 13 shows the results from an in situ hybridization of a mouse brain using probes to detect the presence of Digr1 in the brain.
Figure 13:
Figure 13:
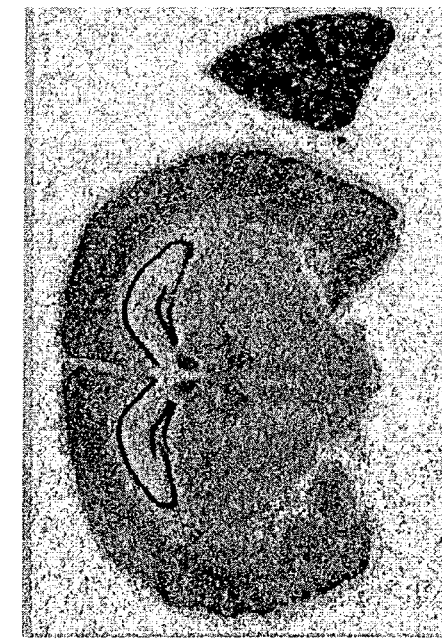
Figure 14:
FIG. 14 shows the results from an in situ hybridization of a mouse brain using probe to detect the presence of Kap10 in the brain.

FIG. 9 is a gel showing immunoprecipitation of Pir-B with polyclonal antibody C19 from whole mouse brain. A Western blot was conducted using either C19 anti-Pir (left) or anti-phosphotyrosine. The results show that Pir-B is phosphorylated in vivo.

The pan specific PIR probe was constructed from the sequence of PIR. The probe is pan specific because the 5' end, about 1800 bp out of 2500 bp, is highly homologous between Pir-A and Pir-B.

The sequence of PIR (SEQ ID NO.: 5) is as follows:
5'-atgtcctgcaccttcacagccctgctct-
gtcttgGACTGACTCTGAGCCT CTGGATCCCAGTGCT-
GACAGggtccctccctaagcctatcctcagagtac agccagactctgtg-
gtctccaggtggactaaggtgactttcttttgtgag
gagacaattggagccaatgagtaccgcctctataaagatggaaagctata
taaaactgtaacaaagaacaaacagaagccagcaaacaaggctgaattct
cactctcaaatgtagacctgagtaatgcaggtcaatatgaatgttcctac agcac-
ccagtataaatcatcaggctacagtgaccccctgaagctggtggt gacaggacac-
tactggacacccagcctttagcccaagccagccctgtgg taacttcaggaggg-
tatgtcaccctccagtgtgagtcctggcacaacgat
cacaagttcattctgactgtagaaggaccacagaagctctcgtggacaca agact-
cacagtataattactctacaaggaagtaccacgccctgttctctg tgggccctgt-
gaccccaaccagagatggatatgcagatgttacagttat gacaggaacagac-
catatgtgtggtcacctccaagtgaatccgtggagct
cctggtctcaggtaatctccaaaaaccaaccatcaaggctgaaccaggat ctgt-
gatcacctccaaaagagcaatgaccatctggtgtcaggggaacctg gatgca-
gaagtatattttctgcataatgagggaagccaaaaaacacagag cacacagac-
cctacagcagcctgggaacaagggcaagttcttcatccctt
ctatgacaagacaacatgcagggcaatatcgctgttattgttacggctca gctggt-
tggtcacagcccagtgacaccctggagctggtggtgacaggaat ctatgaacac-
tataaacccaggctgtcagtactgcccagccctgtggtga cagcaggaggaaa-
catgacactccactgtgcctcagactttcactacgat
aaattcattctcaccaaggaagataagaaattcggcaactcactggacac agag-
catatatcttctagtagacagtaccgagccctgtttattataggac ccacaac-
cccaaccccatacagggacattcagatgttatggttacttcaag aatgcccca-
cagctgtggtcagtacctagtgatctccaacaaatactcat
ctcagggctgtccaagaagccctctctgctgactcaccaaggccatatcc tggac-
cctggaatgaccctcaccctgcagtgttactctgacatcaactat gaca-
gatttgctctgcacaaggtgggggagctgacatcatgcagcactc tagccag-
cagactgacactggcttctctgtggccaacttcacactgggct
atgtgagtagctccactggaggccaatacagatgctatggtgcacacaac ctttc-
ctctgagtggtcagcctccagtgagccctggacatcctgatcac aggacagctc-
cctctcactccttccctctcagtgaagcctaaccacacag tgcactcaggagagac-
cgtgagcctgctgtgttggtcaatggactctgtg
gatctttcattctgtccaaggagggatcagcccagcaaccctacgact aaaat-
caaagtcccatgatcagcagtcccaggcagaattctccatgagtg ctgtgacctc-
ccatctctcagcgacctacaggtgctatggtgctcaaaac tcatctttctacctct-
tgtcatctgccagtgcccctgtggagctcacagt
ctcaggacccatcgaaacctctaccccgccagggacaatgtccatgccac tag-
gtggactgcatatgtacctgaaggctctcattggagtgtctgtgcc ttcatcctgt-
tcctcttcatcctcatcttcattcttctccgacgaagaca tcggggaaaattcag-
gaaagatgtccagaaagagaaagacttgcaactttt
cttcaggagctgaagagcccataaccaggaaaggagaactccagaagagg
cccaacccagctgctgccacccaggaagaaagcctatatgcttcagtgga gga-
catgcaaactgaggatggagtggagctgaacagctggacaccactg aggaa-
gatcccagggagagacttatgcccaggtgaaaccctccaggctc aggaag-
gcaggacatgtctcaccttctgtcatgtcaaggggaacaactgaa
cacagaatatgaacaagcagaagaggggcccaaggagcaaacaatcaggctg
ccgaatctggggagtcccaggatgtgacctatgcccagctgtgcagcagg
acactcagacaggggggcagctgcatctcctctctcccaggcaggggaagc
cccagaggagcccagtgtatatgctactctggcggctgctcgtccagagg ctgt-
tcccaaggatgtggagcaatga-3'

What is claimed is:

1. A method for identifying an agent that interacts with an immune related gene or gene product expressed in nervous tissue selected from the group consisting of Gp49, PIR, PIRA, PIRB, LIR, NKR-P1, NKp46, Digr1, ILT, MIR, KIR, class I MHC molecules, or fragments thereof, or expression products thereof, comprising contacting a candidate agent with the immune related gene, an allele of fragment thereof, or expression product thereof; quantitatively detecting an interaction between said immune related gene an allele of fragment thereof, or expression product thereof and the candidate agent, and separately contacting said candidate agent with neurons expressing said immune related gene in vitro or in vivo, and detecting an alteration in plasticity or activity-dependent remodeling in said neurons.

2. The method of claim 1, wherein said immune related gene expressed in nervous tissue, or fragments thereof, or expression product thereof, or candidate agent comprises a label.

3. The method of claim 1, wherein the immune related gene expressed in nervous tissue, or fragment or expression product thereof is provided on a solid support.

4. The method of claim 1 or 3, wherein binding of the candidate agent with the immune related gene expressed in nervous tissue, or fragment or expression product thereof is detected.

5. The method of claim 1, wherein the alteration is selected from the group consisting of an alteration in neuronal connectivity in neurons expressing said immune related genes, an alteration in an activity-dependent synaptic modification, an alteration in refinement of connections between the retina and a central target during development, and an alteration in long term potentiation or long term depression.

6. The method of claim 1, wherein the candidate agent is a polypeptide, polynucleotide, or small molecule.

* * * * *

UNITED STATES PATENT AND TRADEMARK OFFICE
CERTIFICATE OF CORRECTION

| | | |
|---|---|---|
| PATENT NO. | : 8,071,314 B2 | Page 1 of 1 |
| APPLICATION NO. | : 10/321704 | |
| DATED | : December 6, 2011 | |
| INVENTOR(S) | : Shatz et al. | |

It is certified that error appears in the above-identified patent and that said Letters Patent is hereby corrected as shown below:

In the Specification

Please insert the following text at Column 1, Line number 8:
--GOVERNMENT SUPPORT
This invention was made with government support under MH048108 awarded by the National Institutes of Health. The government has certain rights in the invention.--

Signed and Sealed this
Twenty-eighth Day of January, 2025

Coke Morgan Stewart
*Acting Director of the United States Patent and Trademark Office*